(12) United States Patent
Hofmeister et al.

(10) Patent No.: US 6,339,077 B1
(45) Date of Patent: Jan. 15, 2002

(54) SUBSTITUTED 4-BENZYLAMINOQUINOLINES AND THEIR HETERO ANALOGS, PROCESS FOR THEIR PREPARATION, PHARMACEUTICALS CONTAINING THESE COMPOUNDS AND USE THEREOF

(75) Inventors: Armin Hofmeister, Nierstein; Eugen Falk, Franfurt; Heinz-Werner Kleemann, Bischofsheim; Hans-Willi Jansen, Niedernhausen; Martin Bickel, Bad Homburg, all of (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/667,668

(22) Filed: Sep. 22, 2000

(30) Foreign Application Priority Data

Sep. 22, 1999 (DE) .......................... 199 45 385
Jun. 9, 2000 (DE) .......................... 100 28 193

(51) Int. Cl.⁷ .......................... A61K 31/58; C07J 43/00
(52) U.S. Cl. .................. 514/176; 540/107; 540/113
(58) Field of Search .................. 514/176; 540/107, 540/113

(56) References Cited

U.S. PATENT DOCUMENTS

| | | | |
|---|---|---|---|
| 5,610,151 A | 3/1997 | Glombik et al. | 514/172 |
| 5,641,767 A | 6/1997 | Wess et al. | 874/172 |

FOREIGN PATENT DOCUMENTS

| | | | |
|---|---|---|---|
| EP | 0 624 594 A2 | 11/1994 | |
| EP | 0 676 410 A2 | 10/1995 | |

OTHER PUBLICATIONS

Derwent Abstract 1991–012370 [02], Cholagogic agents for cholaneresis—contg. ursodesoxycholic acid 3–glucuronide, Nov. 26, 1990.
Patent Abstract of Japan for JP 09315979, Cholagogic Agent, Miyazawa Norio, Dec. 9, 1997.
Derwent Abstract 1999–070307 [06], Composition containing new or known benzylamine derivatives—for inhibiting ileal–type bile acid transporter, used for treating hyperlipaemia and arteriosclerosis, Ishihara, S., et al., Dec. 17, 1998.
Martin C. Carey and Donald M. Small, "The Physical Chemistry of Cholesterol Solubility in Bile," *J. Clin. Invest.*, 61:998–1026 (1978).
John C. Sheehan, "A New Method of Forming Peptide Bonds," *J. Am. Chem. Soc.*, 77:1067–1068 (1955).
John C. Sheehan and Joseph J. Hlavka, "The Use of Water–Soluble and Basic Carbodiimides in Peptide Synthesis," *J. Org. Chem.*, 21:439–441 (1956).
H. A. Staab, "New Methods of Preparative Organic Chemistry IV: Syntheses Using Heterocyclic Amides (Azolides)," *Angew. Chem. Internat. Edit.*, 1(7):351–367 (1962).
Augusto C. Veronese et al., "Tin (IV) Chloride–promoted Synthesis of 4–Aminopyridines and 4–Aminoquinolines," *Tetrahedron*, 51(45):12277–12284 (1995).
G. Wess et al., "Modified Bile Acids: Preparation of 7α, 12α–Dihydroxy–3β– And 7α,12α–Dihydroxy–3α–(2–Hydroxyethoxy)–5β–Cholanic Acid and Their Biological Activity," *Tetrahedron Letters*, 33(2):195–198 (1992).
G. Wess et al., "Preparation of 3αa–and 3β–(α–AminoAlkoxy)–7α,12α–Dihydroxy–5β–Cholanoic Acid Esters: Versatile Shuttles For Drug Targeting," *Tetrahedron Letters*, 34(5):817–818 (1993).

*Primary Examiner*—Barbara P. Badio
(74) *Attorney, Agent, or Firm*—Finnegan, Henderson, Farabow, Garrett, & Dunner, L.L.P.

(57) ABSTRACT

The invention relates to substituted 4-benzylaminoquinolines and their hetero analogs, and to the pharmaceutically acceptable salts and physiologically functional derivatives thereof. Compounds of formula I

I

P—L—G in which the radicals are defined in the specification, and their physiologically tolerated salts, physiologically functional derivatives and processes for their preparation are described. The compounds are suitable, for example, as medicines for the prophylaxis or treatment of gallstones.

10 Claims, No Drawings

SUBSTITUTED 4-BENZYLAMINOQUINOLINES AND THEIR HETERO ANALOGS, PROCESS FOR THEIR PREPARATION, PHARMACEUTICALS CONTAINING THESE COMPOUNDS AND USE THEREOF

The invention relates to substituted 4-benzylaminoquinolines and their hetero analogs, and to pharmaceutically acceptable salts and physiologically functional derivatives thereof.

The formation of gallstones is, in addition to a number of factors, essentially determined by the composition of bile, in particular by the concentration and the ratio of cholesterol, phospholipids and bile salts. A precondition for the formation of cholesterol gallstones is the presence of cholesterol-supersaturated bile (Carey, M. C. and Small, D. M.; "The physical chemistry of cholesterol solubility in bile. Relationship to gallstone formation and dissolution in man," *J. Clin. Invest.* 61:998–1026 (1978)).

A great therapeutic demand exists for both the medical dissolution of gallstones and for the prevention of gallstones forming as an alternative to surgical removal of gallstones.

The invention provides compounds which are able to prevent the formation of gallstones by preventing the supersaturation of bile with cholesterol, or by delaying the formation of cholesterol crystals from supersaturated bile.

The invention comprises compounds of formula I:

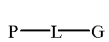

wherein:

G is

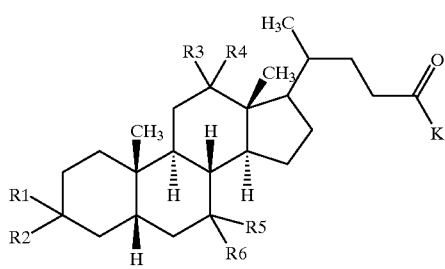

K is —OR(7), —NR(7)R(8), —HN—CH$_2$—CH$_2$—CO$_2$H, —HN—CH$_2$—CH$_2$—SO$_3$H, —NH—CH$_2$—CO$_2$H, —N(CH$_3$)CH$_2$CO$_2$H, —HN—CHR(9)CO$_2$H, or —Ocat, where cat is a cation such as, for example, an alkali metal or alkaline earth metal ion or a quaternary ammonium ion;

R(7), R(8) are independently of one another selected from hydrogen, (C$_1$–C$_4$)-alkyl, phenyl, and benzyl, wherein an aromatic group is optionally substituted from 1 to 3 times by radicals independently of one another selected from F, Cl, CF$_3$, methyl, and methoxy;

R(9) is (C$_1$–C$_4$)-alkyl, benzyl, —CH$_2$—OH, H$_3$CSCH$_2$CH$_2$—, HO$_2$CCH$_2$—, or HO$_2$CCH$_2$CH$_2$—;

R(1) to R(6) are independently of one another selected from hydrogen, —OR(10), —SR(10), —NR(10)R(13), —OCOR(10), —SCOR(10), —NHCOR(10), —OPO(OR(10))$_2$, —OSO$_2$OR(10), —R(10), and one or more pairs of R(1) and R(2), R(3) and R(4), R(5) and R(6), wherein these pairs optionally form a carbonyl group, wherein only one of the radicals R(1) to R(6) is a bond to L;

R(10), R(13) are independently of one another selected from hydrogen, (C$_1$–C$_4$)-alkyl, phenyl, and benzyl, wherein an aromatic group is optionally substituted from 1 to 3 times by radicals independently of one another selected from F, Cl, CF$_3$, methyl, and methoxy;

L is (C$_1$–C$_{15}$)-alkyl, wherein one or more CH$_2$ units is optionally replaced by —CH=CH—, —C≡C—, —NR(11)—, —CO—, —O—, —SO$_2$—, or —S—;

R(11) is hydrogen, (C$_1$–C$_8$)-alkyl, R(12)—CO—, phenyl, or benzyl;

R(12) is hydrogen, (C$_1$–C$_8$)-alkyl, phenyl, or benzyl, wherein an aromatic group is optionally substituted from 1 to 3 times by radicals independently of one another selected from F, Cl, CF$_3$, methyl, and methoxy;

P is

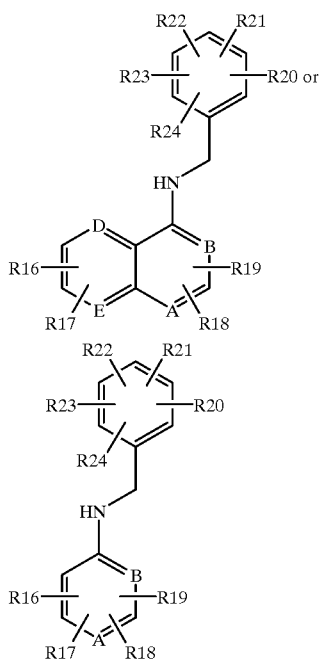

wherein:

A is N or CH;
B is N or CH;
D is N or CH;
E is N or CH;

R(16) to R(24) are independently of one another selected from hydrogen, F, Cl, Br, I, (C$_1$–C$_4$)-alkyl, CN, NO$_2$, NR(25)R(26), OR(25), OCOR(25), COR(25), COOR(25), CONR(25)R(26), SO$_2$R(25), SO$_2$OR(25), and SO$_2$NR(25)R(26), wherein an alkyl radical is optionally substituted one or more times by fluorine, and wherein only one of the radicals R(16) to R(24) is a bond to L; and R(25), R(26) are independently of one another selected from hydrogen, $(C_1-C_4)$-alkyl, phenyl, and benzyl, wherein an alkyl radical is optionally substituted one or more times by fluorine;

or any pharmaceutically acceptable salts or physiologically functional derivatives thereof.

In another embodiment, the compounds of formula I have one or more radical(s) with the following meaning(s):

G is

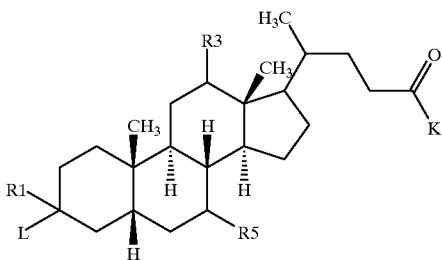

K is OR(7), —NR(7)R(8), —HN—CH$_2$—CH$_2$—CO$_2$H, —HN—CH$_2$—CH$_2$—SO$_3$H, —NH—CH$_2$—CO$_2$H, —N(CH$_3$)CH$_2$CO$_2$H, —HN—CHR(9)CO$_2$H, or —Ocat, where cat is a cation such as, for example, an alkali metal or alkaline earth metal ion or a quaternary ammonium ion;

R(7), R(8) are independently of one another selected from hydrogen, $(C_1-C_4)$-alkyl, phenyl, and benzyl, wherein an aromatic group is optionally substituted from 1 to 3 times by radicals independently of one another selected from F, Cl, CF$_3$, methyl, and methoxy;

R(9) is $(C_1-C_4)$-alkyl, benzyl, —CH$_2$—OH, H$_3$CSCH$_2$CH$_2$—, HO$_2$CCH$_2$—, or HO$_2$CCH$_2$CH$_2$—;

R(1), R(3), R(5) are independently of one another selected from hydrogen, —OR(10), NR(10)R(13), —OCOR(10), and —NHCOR(10);

R(10), R(13) are independently of one another selected from hydrogen, $(C_1-C_4)$-alkyl, phenyl, and benzyl, wherein an aromatic group is optionally substituted from 1 to 3 times by radicals independently of one another selected from F, Cl, CF$_3$, methyl, and methoxy;

L is $(C_1-C_8)$-alkyl, wherein one or more CH$_2$ units is optionally replaced by —CH=CH—, —C≡C—, —NR(11)—, —CO—, —O—, or —SO$_2$—;

R(11) is hydrogen, $(C_1-C_4)$-alkyl, R(12)—CO—, phenyl, or benzyl;

R(12) is hydrogen, $(C_1-C_4)$-alkyl, phenyl, or benzyl, wherein an aromatic group is optionally substituted from 1 to 3 times by radicals independently of one another selected from F, Cl, CF$_3$, methyl, and methoxy;

P is

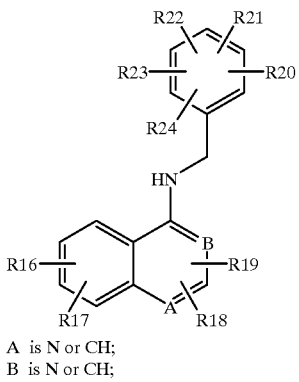

A is N or CH;
B is N or CH;

R(16) to R(24) are independently of one another selected from hydrogen, F, Cl, Br, $(C_1-C_4)$-alkyl, NR(25)R(26), OR(25), OCOR(25), COR(25), COOR(25), and CONR(25)R(26), wherein an alkyl radical is optionally substituted one or more times by fluorine, and wherein only one of the radicals R(16) to R(24) is a bond to L; and R(25), R(26) are independently of one another selected from hydrogen, $(C_1-C_4)$-alkyl, phenyl, and benzyl, wherein an alkyl radical is optionally substituted one or more times by fluorine;

or any pharmaceutically acceptable salts or physiologically functional derivatives thereof.

Compounds of formula I are found in yet another embodiment in which one or more radical(s) has or have the following meaning(s):

G is

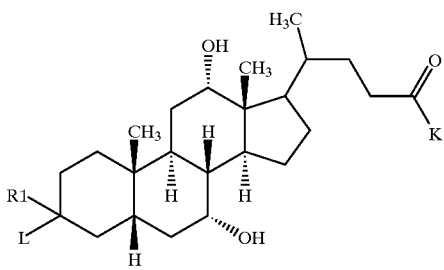

K is —OR(7), —NR(7)R(8), —HN—CH$_2$—CH$_2$—CO$_2$H, —HN—CH$_2$—CH$_2$—SO$_3$H, —NH—CH$_2$—CO$_2$H, —N(CH$_3$)CH$_2$CO$_2$H, or —Ocat, where cat is a cation such as, for example, an alkali metal or alkaline earth metal ion or a quaternary ammonium ion;

R(7), R(8) are independently of one another selected from hydrogen, $(C_1-C_4)$-alkyl, phenyl, and benzyl, wherein an aromatic group is optionally substituted from 1 to 3 times by radicals independently of one another selected from F, Cl, CF$_3$, methyl, and methoxy;

R(1) is hydrogen, or —OH;

L is (C₁–C₅)-alkyl, wherein one or more CH₂ units is optionally replaced by —CH=CH—, —C≡C—, —NR(11)—, —CO—, —O—, or —SO₂—;

R(11) is hydrogen, (C₁–C₄)-alkyl, R(12)—CO—, phenyl, or benzyl;

R(12) is hydrogen, (C₁–C₄)-alkyl, phenyl, or benzyl, wherein an aromatic group is optionally substituted from 1 to 3 times by radicals independently of one another selected from F, Cl, CF₃, methyl, and methoxy;

P is

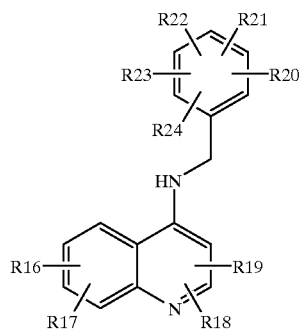

R(16) to R(24) are independently of one another selected from hydrogen, F, Cl, (C₁–C₄)-alkyl, NR(25)R(26), OR(25), OCOR(25), COR(25), COOR(25), and CONR(25)R(26), wherein an alkyl radical is optionally substituted one or more times by fluorine, and wherein only one of the radicals R(16) to R(24) is a bond to L; and R(25), R(26) are independently of one another selected from hydrogen, (C₁–C₄)-alkyl, phenyl, and benzyl, wherein an alkyl radical is optionally substituted one or more times by fluorine;

or any pharmaceutically accept able salt thereof.

Of further interest are compounds of formula I in which one or more radicals have the following meaning(s):

G is

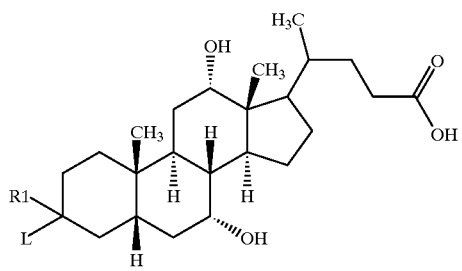

R(1) is hydrogen or —OH; p2 L is (C₁–C₅)-alkyl, wherein one or more CH₂ units is optionally replaced by —CH=CH—, —C≡C—, —NR(11)—, —CO—, —O—, or —SO₂—;

P is

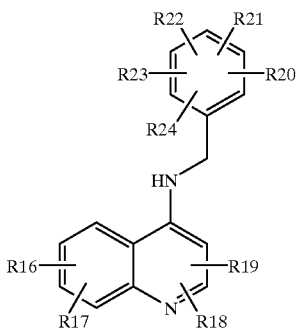

wherein:

R(16) to R(24) are independently of one another selected from hydrogen, F, Cl, (C₁–C₄)-alkyl, NR(25)R(26), OR(25), OCOR(25), COR(25), COOR(25), and CONR(25)R(26), wherein an alkyl radical is optionally substituted one or more times by fluorine, and wherein only one of the radicals R(16) to R(24) is a bond to L; and R(25), R(26) are independently of one another selected from hydrogen, (C₁–C₄)-alkyl, phenyl, and benzyl, wherein an alkyl radical is optionally substituted one or more times by fluorine;

or any pharmaceutically acceptable salt thereof.

If the compounds of formula I contain one or more centers of asymmetry, these may have either the S or the R configuration. The compounds may be in the form of optical isomers, diastereomers, racemates or mixtures thereof.

The expression "wherein an alkyl radical is optionally substituted one or more times by fluorine" also includes perfluorinated alkyl radicals. Alkyl radicals may be either straight-chain or branched.

Pharmaceutically acceptable salts, by reason of their greater solubility in water compared with the initial or basic compounds, are particularly suitable for medical applications. These salts must have a pharmaceutically acceptable anion or cation. Suitable pharmaceutically acceptable acid addition salts of the novel compounds are salts of inorganic acids such as hydrochloric, hydrobromic, phosphoric, metaphosphoric, nitric, sulfamic, and sulfuric acid, and organic acids such as acetic, benzenesulfonic, benzoic, citric, ethanesulfonic, fumaric, gluconic, glycolic, isethionic, lactic, lactobionic, maleic, malic, methanesulfonic, succinic, p-toluenesulfonic, tartaric, and trifluoroacetic acid. It is preferred to use the chloride salt for medical purposes. Suitable pharmaceutically acceptable basic salts are ammonium salts, alkali metal salts (such as sodium and potassium salts) and alkaline earth metal salts (such as magnesium and calcium salts).

Salts with a pharmaceutically unacceptable anion likewise belong within the framework of the invention as useful intermediates for the preparation or purification of pharmaceutically acceptable salts and/or for use in nontherapeutic, for example in vitro, applications.

The term "physiologically functional derivative" used herein designates any physiologically tolerated derivative of a compound of formula I, for example an ester, which is able on administration to a mammal such as, for example, a human to form (directly or indirectly) a compound of formula I or an active metabolite thereof.

The physiologically functional derivatives include prodrugs of the instant inventive compounds. Such prodrugs can be metabolized in vivo to one of the instant inventive compounds. These prodrugs may or may not themselves have activity.

The compounds of the invention may also exist in various polymorphous forms, for example as amorphous and crystalline polymorphous forms. All polymorphous forms of the compounds of the invention form part of the invention and are a further aspect of the invention.

All references to "compound(s) of formula I" hereinafter refer to compound(s) of formula I as described above, and their salts, solvates and physiologically functional derivatives as described herein.

The amount of a compound of formula I necessary to achieve the desired biological effect depends on a number of factors, such as the specific compound chosen, the intended use, the mode of administration, and the clinical condition of the patient.

The daily dose is generally in the range from 0.1 mg to 100 mg (typically from 0.1 mg to 50 mg) per day and per kilogram body weight, for example from 0.1 to 10 mg/kg/day. Tablets or capsules may contain dosages, for example, from 0.01 to 100 mg, typically from 0.02 to 50 mg. In the case of pharmaceutically acceptable salts, the aforementioned weight data relate to the weight of the salt of the compound of formula I.

For prophylaxis or therapy of the above mentioned conditions, compounds of formula I can be used directly as the compound itself, but are preferably used in the form of a pharmaceutical composition with a compatible carrier. The carrier must, of course, be compatible in the sense that it is compatible with the other ingredients of the composition and is not harmful to the patient's health. The carrier may be a solid or a liquid or both and is preferably formulated with the compound as single dose, for example as a tablet which may contain from 0.05% to 95% by weight of the active ingredient.

Further pharmaceutically active substances may likewise be present, including further compounds of formula I. The pharmaceutical compositions of the instant invention can be produced by one of the known pharmaceutical methods which consist essentially of mixing the ingredients with pharmacologically acceptable carriers and/or excipients.

Pharmaceutical compositions of the invention are those suitable for oral and peroral (for example sublingual) administration although the most suitable mode of administration depends in each individual case on the nature and severity of the condition to be treated and on the nature of the particular compound of formula I used. The invention also embraces coated formulations and coated slow-release formulations. Formulations resistant to acid and gastric fluid are preferred. Suitable coatings resistant to gastric fluid comprise cellulose acetate phthalate, polyvinyl acetate phthalate, hydroxypropylmethylcellulose phthalate, and anionic polymers of methacrylic acid methyl methacrylate.

Suitable pharmaceutical compounds for oral administration may be in the form of separate units such as capsules, cachets, pastilles, or tablets, each of which contains a defined amount of a compound of formula I; as powders or granules; as solution or suspension in an aqueous or non-aqueous liquid; or as an oil-in-water or water-in-oil emulsion. These compositions can, as already mentioned, be prepared by any suitable pharmaceutical method which includes a step in which the active ingredient and the carrier (which may consist of one or more additional ingredients) are brought into contact. In general, the compositions are produced by uniform and homogeneous mixing of the active ingredient with a liquid and/or finely dispersed solid carrier, after which the product is shaped if necessary. Thus, for example, a tablet can be produced by compressing or shaping a powder or granules of the compound, where appropriate with one or more additional ingredients. Compressed tablets can be produced by tableting the compound in free-flowing form, such as, for example, a powder or granules, and where appropriate, mixed with a binder, lubricant, inert diluent and/or one (or more) surface-active/dispersing agents in a suitable machine. Shaped tablets can be produced by shaping, in a suitable machine, the compound which is in powder form and has been moistened with an inert liquid diluent.

Pharmaceutical compositions suitable for peroral (sublingual) administration comprise suckable tablets which contain a compound of formula I with a flavoring, normally sucrose, and gum arabic or tragacanth, and pastilles which comprise the compound in an inert base such as gelatin and glycerol or sucrose and gum arabic.

The invention further relates to two processes for preparing the compounds of formula I.

Process A) This entails a compound of formula IIId, where X is halogen, such as Br or I, being reacted with a compound of formula IId in a Pd(0)-catalyzed coupling reaction. The HX liberated thereby is trapped by an auxiliary base (such as triethylamine or pyridine).

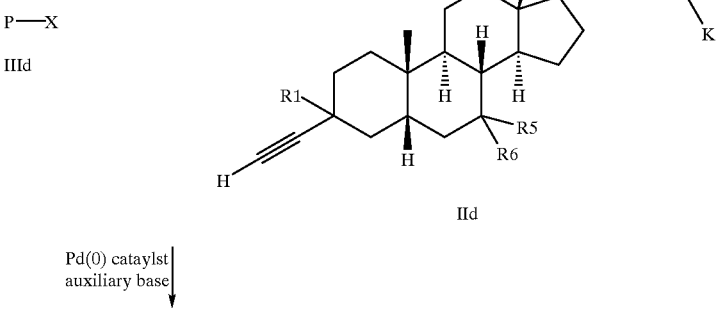

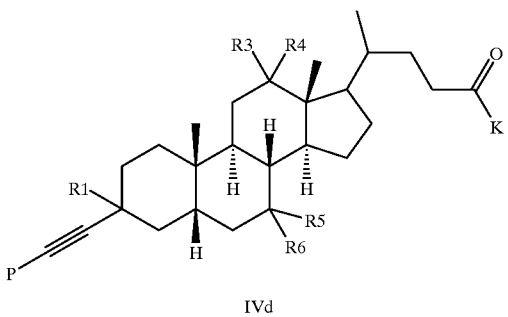

IVd

R1, R3, R4, R5, K and P are defined as above. The ethynyl-bile acid derivatives of formula IId are prepared from suitable bile acid ketones. For this purpose, lithium acetylide is added onto keto-bile acids analogously to known processes (U.S. Pat. No. 5,641,767).

Process B) Carboxylic acids of formula IIIe (R=OH) are reacted with compounds of formula IIe in a known manner in the presence of suitable coupling reagents such as, for example, TOTU (*Chemiker Zeitung*, 98:817(1974)), DCC/HOBt (*J. Am. Chem. Soc.*, 77:1067 (1955)), or CMC/HOBt (*J. Org. Chem.*, 21:439 (1956)), (see abbreviations below) forming an amide linkage. Carboxamides of formula IVe may also be formed by reacting activated carboxylic acid derivatives IIIe with compounds of formula IIe in the presence of an auxiliary base (for example, triethylamine or pyridine) in a manner known to the skilled worker. Exemplary activated carboxylic acid derivatives of formula IIe are the corresponding chlorides (R=Cl), imidazolides (R=1-imidazolyl; *Angew. Chem. Int. Ed. Engl.*, 1:351 (1962)), or the mixed anhydrides with Cl—COOEt or tosyl chloride.

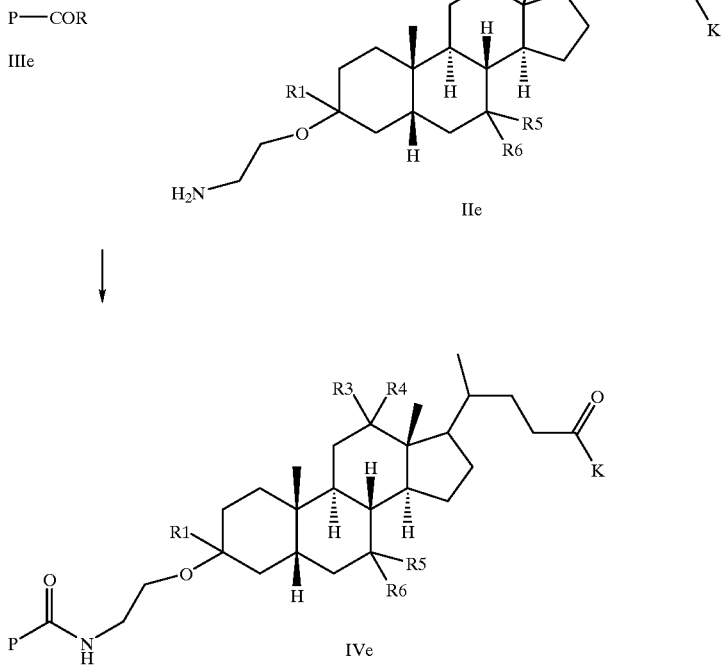

R1, R3, R4, R5, K and P are defined as above. The 3-ethanolamine-bile acid building blocks of formula IIe are prepared by known processes (*Tetrahedron Lett.*, 34:817 (1993)).

Compounds of formula I and their pharmaceutically acceptable salts and physiologically functional derivatives have a beneficial effect on the composition of bile and prevent the formation of gallstones by preventing supersaturation of the bile with cholesterol, or by delaying the formation of cholesterol crystals from supersaturated bile. Compounds of the present invention can be employed alone or in combination with lipid-lowering active ingredients (see *Rote Liste*, chapter 58). The inventive compounds are particularly suitable for the prophylaxis and for the treatment of gallstones.

Compounds of formula I enter the hepatobiliary system and therefore act in these tissues. Thus, the absorption of water from the gall bladder is inhibited through inhibition of the apical NHE antiport of subtype 3 of the gall bladder epithelium, which results in a diluted bile.

Biological testing of the novel compounds was accomplished by measuring inhibition of the sodium/proton exchanger subtype 3.

1. Test Description

The remaining activity of the human NHE-3 protein (expressed in the LAP1 cell line) was determined by measuring the recovery in the intracellular pH ($pH_i$) after an acidification, which starts when the NHE is capable of functioning, even under bicarbonate-free conditions. For this purpose, the $pH_i$ was determined using the pH-sensitive fluorescent dye BCECF (Calbiochem, the precursor BCECF-AM is employed). The cells were initially loaded with BCECF. The BCECF fluorescence was determined in a "ratio fluorescence spectrometer" (Photon Technology International, South Brunswick, N.J., USA) with excitation wavelengths of 505 and 440 nm and an emission wavelength of 535 nm, and was converted into the $pH_i$ using calibration plots. The cells were incubated in $NH_4Cl$ buffer (pH 7.4) ($NH_4Cl$ buffer: 115 mM NaCl, 20 mM $NH_4Cl$, 5 mM KCl, 1 mM $CaCl_2$, 1 mM $MgSO_4$, 20 mM HEPES, 5 mM glucose, 1 mg/ml BSA; a pH of 7.4 is adjusted with 1 M NaOH) even during the BCECF loading. The intracellular acidification was induced by addition of 975 µl of an $NH_4Cl$-free buffer (see below) to 25 µl aliquots of the cells incubated in $NH_4Cl$ buffer. The subsequent rate of pH recovery was recorded for 3 minutes. To calculate the inhibitory power of the substances tested, the cells were initially investigated in buffers in which complete or absolutely no pH recovery took place. For complete pH recovery (100%), the cells were incubated in $Na^+$-containing buffer (133.8 mM NaCl, 4.7 mM KCl, 1.25 mM $CaCl_2$, 1.25 mM $MgCl_2$, 0.97 mM $Na_2HPO_4$, 0.23 mM $NaH_2PO_4$, 5 mM HEPES, 5 mM glucose, a pH of 7.0 was adjusted with 1 M NaOH). To determine the 0% value, the cells were incubated in an $Na^+$-free buffer (133.8 mM choline chloride, 4.7 mM KCl, 1.25 mM $CaCl_2$, 1.25 mM $MgCl_2$, 0.97 mM $K_2HPO_4$, 0.23 mM $KH_2PO_4$, 5 mM HEPES, 5 mM glucose, a pH of 7.0 was adjusted with 1 M NaOH). Test solutions of the substances of interest were made up in the $Na^+$-containing buffer. Recovery of the intracellular pH at the tested concentration of a substance was expressed as a percentage of the maximum recovery.

Results:
Example 1: remaining activity of hNHE3 at 30 µM=26%
Example 2: remaining activity of hNHE3 at 30 µM=33%
Example 3: remaining activity of hNHE3 at 30 µM=22%
Example 6: remaining activity of hNHE3 at 30 µM=39%
Example 11: remaining activity of hNHE3 at 30 µM=61%
Example 13: remaining activity of hNHE3 at 30 µM=40%
Example 14: remaining activity of hNHE3 at 30 µM=52%
Example 15: remaining activity of hNHE3 at 30 µM=65%
Example 16: remaining activity of hNHE3 at 30 µM=27%
Example 17: remaining activity of hNHE3 at 30 µM=36%
Example 18: remaining activity of hNHE3 at 30 µM=36%
Example 20: remaining activity of hNHE3 at 30 µM=56%
Example 23: remaining activity of hNHE3 at 30 µM=16%
Example 24: remaining activity of hNHE3 at 30 µM=29%
Example 25: remaining activity of hNHE3 at 30 µM=18%
Example 26: remaining activity of hNHE3 at 30 µM=52%
Example 27: remaining activity of hNHE3 at 30 µM=54%
Example 28: remaining activity of hNHE3 at 30 µM=69%
Example 29: remaining activity of hNHE3 at 30 µM=61%
Example 30: remaining activity of hNHE3 at 30 µM=48%
Example 31: remaining activity of hNHE3 at 30 µM=69%

List of abbreviations:

| | |
|---|---|
| Me | methyl |
| LAH | lithium aluminum hydride |
| DMF | N,N-dimethylformamide |
| EI | electron impact |
| CI | chemical ionization |
| RT | room temperature |
| EA | ethyl acetate |
| mp | melting point |
| HEP | n-heptane |
| DME | dimethoxyethane |
| ES | electron spray |
| FAB | fast atom bombardment |
| THF | tetrahydrofuran |
| eq. | Equivalent |
| TOTU | O-[(ethoxycarbonyl)cyanomethyleneamino]-N,N,N',N'-tetramethyluronium tetrafluoroborate |
| HOBt | 1-hydroxybenzotriazole |
| CMC | N-cyclohexyl-N'-(2-morpholinoethyl)carbodiimide metho-p-toluenesulfonate |
| DCC | dicyclohexylcarbodiimide |

The following examples serve to illustrate the invention in detail without restricting the latter to products and embodiments described in the examples.

EXAMPLE 1

2-Methyl-3-acetyl-4-{4-[1-(3α,7α, 12α-trihydroxy-10β, 13β-dimethyl-17β-(carboxy-1-methylpropyl)hexadecahydrocyclopenta[a]phenanthren-3-yl)ethyn-2-yl]-benzylamino}quinoline

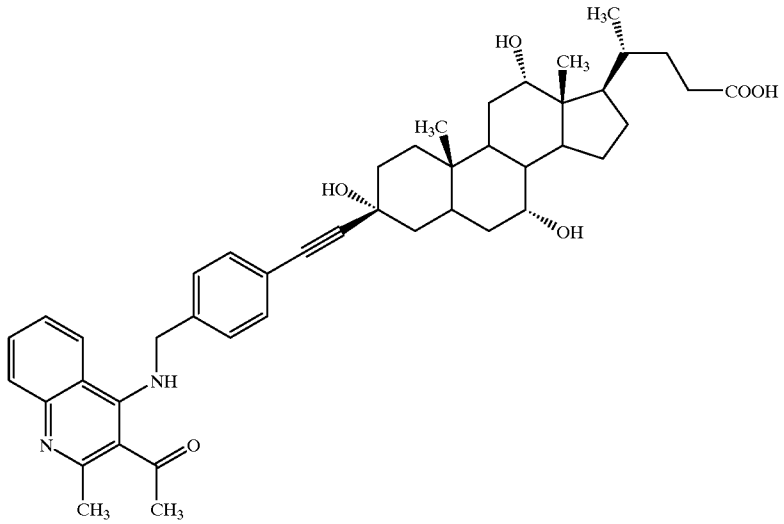

Preparation of Intermediates:

Intermediate 1: 3β-Ethynylcholic Acid

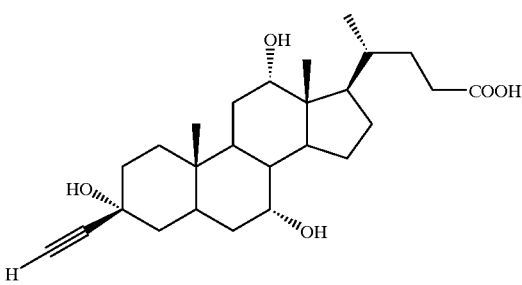

Synthetic route:

a) Methyl 3,7,12-triacetylcholate 90 g of methyl cholate and 3.0 g of dimethylaminopyridine were dissolved in 500 ml of pyridine and, after addition of 500 ml of acetic anhydride, stirred at room temperature overnight. The mixture was poured into ice water and extracted three times with ethyl acetate. Drying with MgSO$_4$ and evaporation of the organic phase afforded 92 g of methyl 3,7,12-triacetylcholate, MS(FAB): M$^+$+Li=555.

b) Methyl 7,12-diacetylcholate

At 5° C., 150 ml of acetic anhydride were slowly added dropwise to 1.5L of methanol. After 15 minutes, 92 g of methyl 3,7,12-triacetylcholate were added, and the mixture was stirred at room temperature for 1 h. It was poured into ice-water and extracted three times with ethyl acetate. The organic phase was washed with 1N Na$_2$CO$_3$ solution, dried with MgSO$_4$ and evaporated. 85 g of crude product were obtained, MS(FAB): M$^+$+Li=513.

c) Methyl 3-keto-7,12-diacetylcholate 85 g (168 mmol) of methyl 7,12-diacetylcholate, 183.7 g of pyridinium chlorochromate and 175 g of molecular sieves were stirred in 2.5 L of dichloromethane, at room temperature for 2 h. The mixture was poured into 7 L of diethyl ether, and the solids were filtered off. The solvent was evaporated and the residue was dissolved in ethyl acetate. Chromatography on a Florisil column resulted in 59.6 g of product, MS(FAB): M$^+$+Li=511.

d) Methyl 3β-ethynyl-7,12-diacetylcholate

Acetylene was passed into 750 ml of abs. tetrahydrofuran at −55° C. under argon for 25 min. 145 ml of 15% n-butyllithium in hexane were added dropwise to this solution, followed by stirring for 10 min. Then 45 g (89 mmol) of methyl 3-keto-7,12-diacetylcholate were added and the mixture was stirred at −40° C. for 1.5 h. For workup, 500 ml of saturated aqueous ammonium chloride solution were added and, after extraction three times with ethyl acetate, the organic phase was dried over MgSO$_4$ and evaporated. The residue was chromatographed on silica gel (n-heptane/ethyl acetate 1:1). 35.3 g of product were obtained, MS(FAB): M$^+$+Li=537.

e) 3β-Ethynylcholic Acid 35.2 g (66 mmol) of the product from d) were dissolved in 1 L of methanol and, after addition of 300 ml of 2N sodium hydroxide solution, heated under reflux for 25 h. The solvent was evaporated, and the residue was dissolved in water and acidified to pH 2 with 2N hydrochloric acid. The precipitate was filtered off and washed with water to neutrality. Drying of the residue afforded 14.6 g of product, MS(FAB): M$^+$+Li=439.

Intermediate 2: 2-Methyl-3-acetyl-4-(4-bromobenzylamino)quinoline

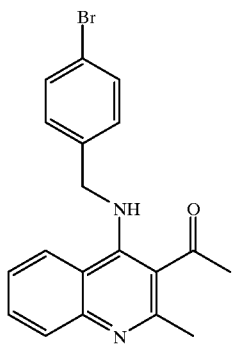

Synthetic Route a) 2-(1-Methyl-3-oxobut-1-enylamino)benzonitrile was prepared by standard methods from 2-aminobenzonitrile (Eur. Pat. Appl., C07D 215/42; *J. Med. Chem.*, 31:1278 (1988)); yellow solid, melting point: 100° C.; MS(Cl): M$^+$+H=201.

b) 1-(4-Amino-2-methylquinolin-3-yl)ethanone was prepared by a known process, starting from 2-(1-methyl-3-oxobut-1-enylamino)benzonitrile, by cyclization with CuCl and K$_2$CO$_3$ (*J. Med. Chem.*, 31:1278 (1988)) or by a NaOMe-promoted process (Eur. Pat. Appl., C07D 215/42); yielding a yellow solid; MS(Cl): M$^+$+H=201.

c) 1-(4-(4-Bromobenzylamino-2-methylquinolin-3-yl) ethanone In a two-phase system consisting of 75 ml of CH$_2$Cl$_2$ and 55 ml of 50% strength NaOH, 1.8 g of 1-(4-amino-2-methylquinolin-3-yl)ethanone were mixed with 0.15 eq of tetrabutylammonium hydrogen sulfate and vigorously stirred at room temperature for 30 min. Then 1.1 eq of 4-bromobenzyl bromide were added and the mixture was vigorously stirred at room temperature for 4 to 5 h. For workup, the two phases were separated, the aqueous phase was then extracted twice with CH$_2$Cl$_2$, and the combined organic phases were then washed twice with H$_2$O and dried with MgSO$_4$. The solvent was distilled off and the residue was purified on silica gel (300 g; CH$_2$Cl$_2$MeOH 98:2), resulting in the title compound as a colorless glassy solid. MS(ES+): M$^+$+H=369.

General Method for the Pd(0)-catalyzed Coupling Reaction

The bromoaryl compound (1.0 eq) and the bile acid-acetylene building block (1.5 eq) were introduced into DMF/triethylamine (2:1) and the solution was degassed. After flushing with argon, 0.1 eq of Pd(PPh$_3$)$_2$Cl$_2$ and 0.1 eq of CuI were added and the reaction solution was heated to 80° C. Depending on the progress of the reaction it was optionally worthwhile to add further catalyst or raise the temperature further, possibly up to 100° C. For workup, the solvent was removed and the crude product obtained was purified on silica gel with a CH$_2$Cl$_2$/MeOH mixture.

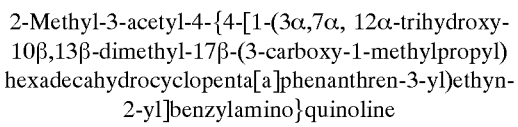

Carrying out the reaction by the general method afforded after 21 h at 100° C., a yellow-orange solid, melting point: 178° C. (decomposition), MS(ES+): M$^+$+H=772.

EXAMPLE 2

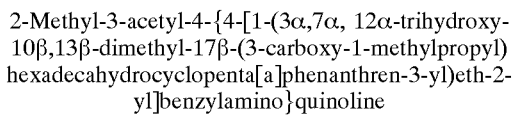

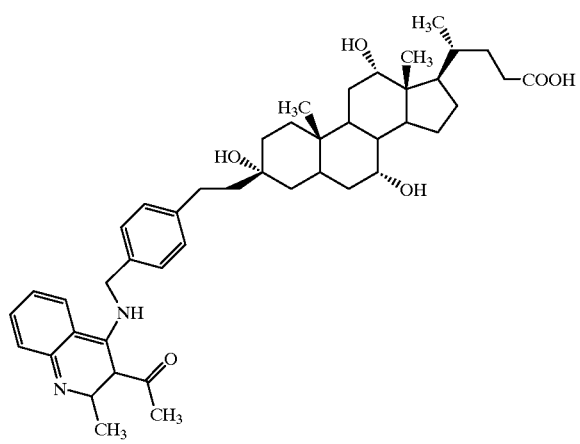

The product obtained above from Example 1 was dissolved in 1:1 ethanol/methanol and, after addition of Pd/C (10%), shaken under an H$_2$ atmosphere until the conversion was complete. Removal of the Pd catalyst by filtration, and of the solvent by distillation, provided the hydrogenated product as a yellowish crystalline solid. Melting point: 172° C. (decomposition); MS(ES+): M$^+$+H=726.

EXAMPLE 3

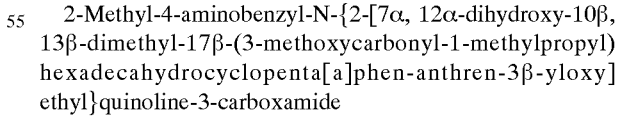

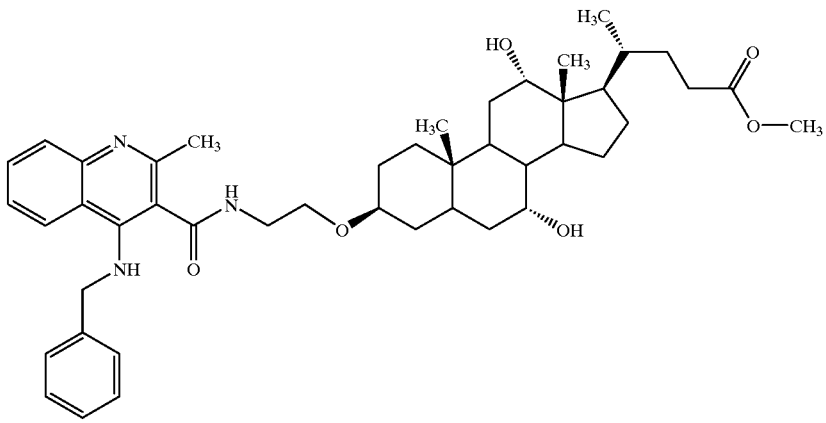

Preparation of Intermediates:
Intermediate 1: Methyl 3β-(2-aminoethoxy)cholate

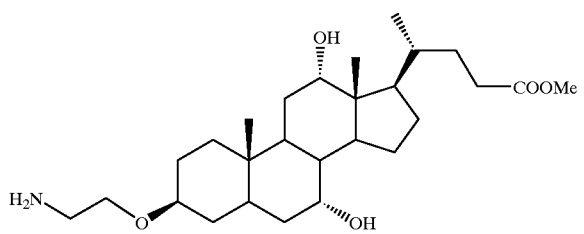

The title compound was prepared in a manner known from the literature starting from cholic acid in six steps (*Tetrahedron Lett.*, 33:195 (1992), *Tetrahedron Lett.*, 34:817 (1993)).

Intermediate 2: 4-Benzylamino-2-methylquinoline-3-carboxylic Acid

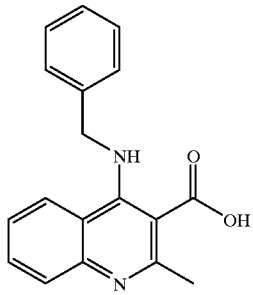

Synthetic Route:
a) Methyl 4-amino-2-methylquinoline-3-carboxylate was prepared by a published method (*Tetrahedron*, 51:12277 (1995)). MS(Cl): $M^++H=217$.
b) Methyl 4-benzylamino-2-methylquinoline-3-carboxylate was synthesized by the same method as described for 1-(4-(4-bromobenzylamino-2-methylquinolin-3-yl)ethanone (Example 1, Intermediate 2c) starting from methyl 4-amino-2-methylquinoline-3-carboxylate and benzyl bromide. MS(ES+): $M^++H=307$.
c) 4-Benzylamino-2-methylquinoline-3-carboxylic acid was prepared by hydrolyzing the methyl ester with KOH (5 eq) in ethanolic solution. After conversion was complete, the solvent was removed and the crude product was taken up in 2N NaOH. The aqueous solution was extracted with $CH_2Cl_2$, the phases were separated and the aqueous phase was neutralized with 2N HCl, whereupon the title compound precipitated. Filtering off and drying provided a colorless solid. Melting point: 190° C.; MS(Cl): $M^++H=293$, $M^+-CO_2=249$.

2-Methyl-4-aminobenzyl-N-{2-[7α,12α-dihydroxy-10β, 13β-dimethyl-17β-(3-methoxycarbonyl-1-methylpropyl) hexadecahydrocyclopenta[a]phenanthren-3β-yloxy] ethyl}quinoline-3-carboxamide as trifluoroacetate.

Intermediate 1 (1.0 eq) and intermediate 2 (1.0 eq) were introduced into DMF and, after addition of 1.0 eq of HOBt, at 0° C. a solution of 1.1 eq of CMC in DMF is added. If necessary, additional CMC was added and/or the temperature was increased, possibly up to 60° C. For workup, the solvent was removed, and the residue was taken up in ethyl acetate and washed twice with saturated $NaHCO_3$. The $NaHCO_3$ phases were extracted once more with ethyl acetate, and the combined organic extracts were washed twice with $H_2O$, dried with $MgSO_4$, and evaporated. The crude product obtained was purified by preparative HPLC, resulting in the title compound as a pale yellowish solid. Melting point: 102° C.; MS(ES+): $M^++H=741$.

EXAMPLE 4

2-Methyl-4-aminobenzyl-N-{2-[7α,12α-dihydroxy-10β,13β-dimethyl-17β-(3-carboxy-1-methylpropyl) hexadecahydrocyclopenta[a]phenanthren-3β-yloxy]-ethyl}quinoline-3-carboxamide

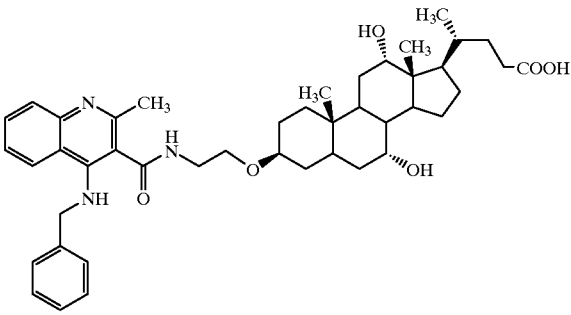

The product from Example 3 was mixed with 5.0 eq of KOH in a methanol/$H_2O$ mixture and stirred at a temperature between room temperature and 50° C. If necessary, additional KOH was added until complete conversion was reached. The solvent was then removed, and the residue was taken up in H₂O and neutralized with 1 N HCl. The resulting precipitate was filtered off then dried, resulting in the product as a colorless solid. Melting point: 143° C.; MS(ES+): M⁺+H=727.

EXAMPLE 5

2-Methyl-4-aminobenzyl-N-{2-[7α,12α-dihydroxy-10β,13β-dimethyl-17β-(3-(2-sulfoethyl)carbamoyl-1-methylpropyl)hexadecahydrocyclopenta[a]-phenanthren-3β-yloxy]ethyl}quinoline-3-carboxamide as trifluoroacetate 85 mg of the product acid from Example 3 were dissolved in 5 ml of abs. DMF. At 0° C., a solution of 0.016 ml of NEt₃ in 1 ml of abs. DMF was added, and 1.0 eq of TOTU dissolved in 2 ml of abs. DMF was added dropwise. After stirring at between 0° C. and room temperature for 1 h, the resulting solution was added to a mixture of 1.0 eq of taurine, 1 ml of NEt₃, 2 ml of H₂O and 2 ml of DMF and stirring was continued. For workup, the reaction mixture was concentrated and purified by preparative HPLC, resulting in the title compound as a yellowish solid. Melting point: 180° C.; MS(ES+): M⁺+H=834.

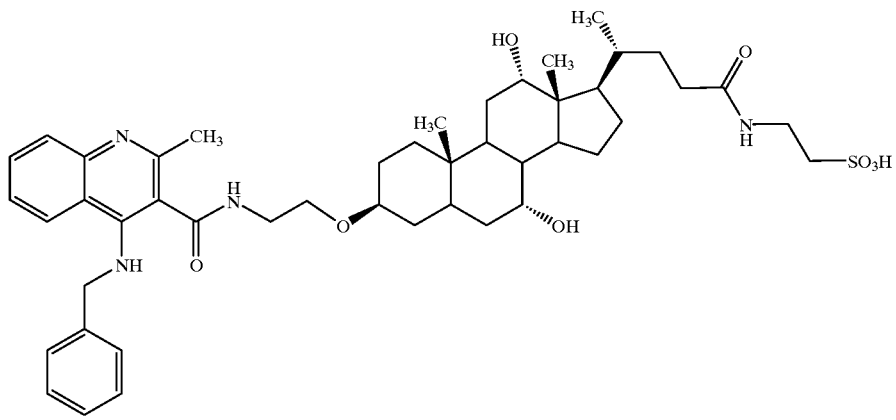

EXAMPLE 6

Methyl 2-methyl-4-{4-[1-(3α,7α,12α-trihydroxy-10β, 13β-dimethyl-17β-(3carboxy-1-methylpropyl)hexadecahydrocyclopenta[a]phenanthren-3-yl)ethyn-2-yl]benzylamino}quinoline-3-carboxylate

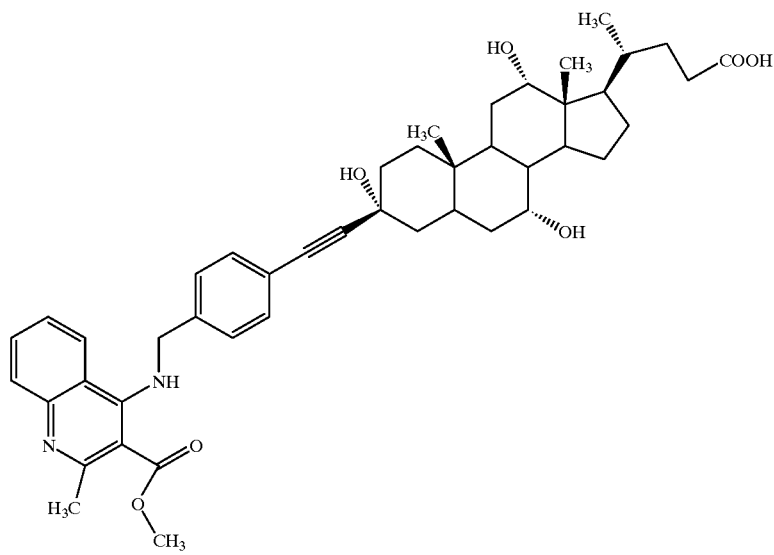

Preparation of Intermediates:
Intermediate 1: 3β-Ethynylcholic Acid

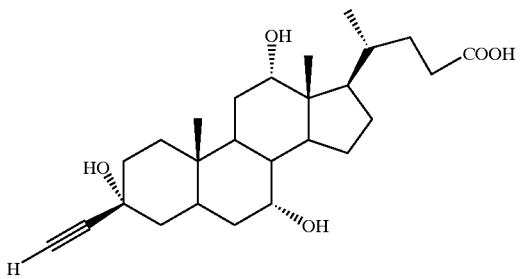

see Example 1

Intermediate 2: Methyl 4-(4-bromobenzylamino)-2-methylquinoline-3-carboxylate

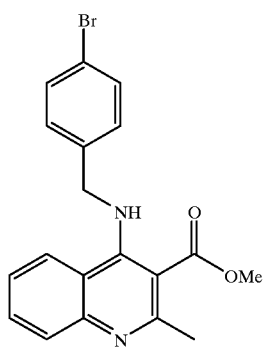

Synthetic Route:

a) Methyl 4-amino-2-methylquinoline-3-carboxylate was prepared in a manner known to the skilled worker (*Tetrahedron* 51:12277 (1995)).

b) Methyl 4-(4-bromobenzylamino)-2-methylquinoline-3-carboxylate was synthesized by the same method as described for 1-(4-(4-bromobenzylamino-2-methylquinolin-3-yl)ethanone (Example 1, Intermediate 2c), starting from methyl 4-amino-2-methylquinoline-3-carboxylate and 4-bromobenzyl bromide. Melting point: 89° C.; MS(ES+): 385/387.

Methyl 2-methyl-4-{4-[1-(3α,7α,12α-trihydroxy-10β,13β-dimethyl-17β-(3-carboxy-1-methylpropyl)hexadecahydrocyclopenta[a]phenanthren-3-yl)ethyn-2-yl]benzylamino}quinoline-3-carboxylate was prepared by the general process indicated (see Example 1). Melting point: 165° C.; MS(FAB): 737.

EXAMPLE 7 n-Butyl 2-methyl-4-{4-[1-(3α,7α,12α,trihydroxy-10β,13β-dimethyl-17β-(3-carboxy-1-methylpropyl)hexadecahydrocyclopenta[a]phenanthren-3-yl)ethyn-2-yl]benzylamino}quinoline-3-carboxylate

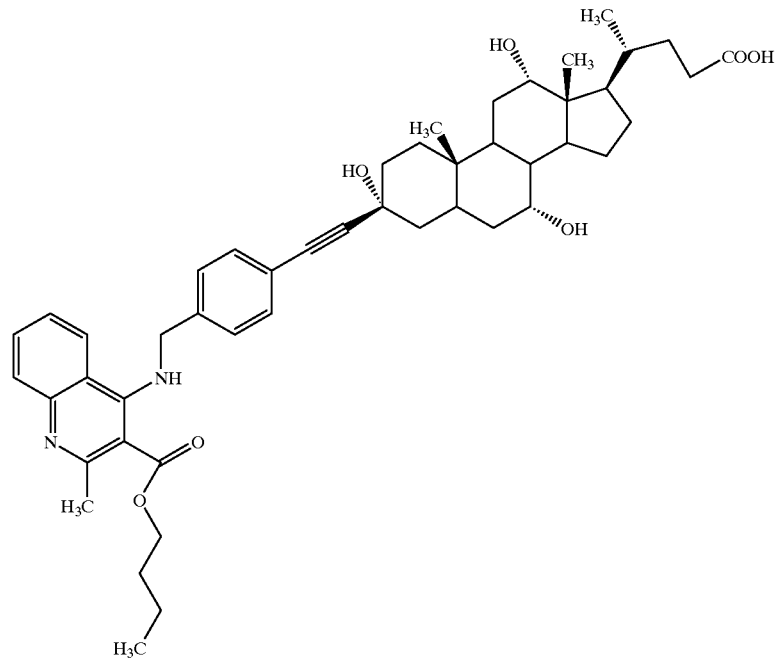

Preparation of Intermediates:
Intermediate 1: 3β-Ethynylcholic Acid

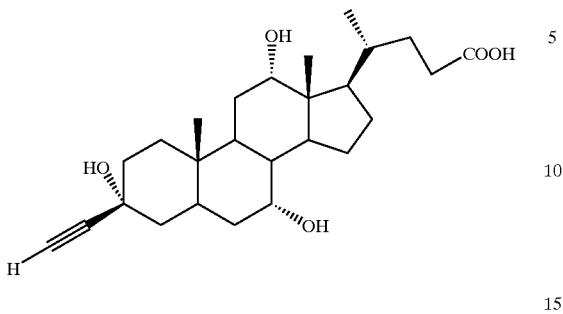

see Example 1

Intermediate 2: n-Butyl 4-(4-bromobenzylamino)-2-methylquinoline-3-carboxylate

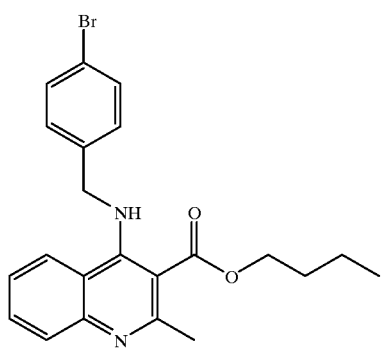

Synthetic Route:

a) n-Butyl 4-(4-bromobenzylamino)-2-methylquinoline-3-carboxylate 200 mg (1.0 eq) of methyl 4-(4-bromobenzylamino)-2-methylquinoline-3-carboxylate (see Example 5) were dissolved in an n-butanol/THF mixture and, at room temp., 2.5 eq of NaH (55%) were added and the mixture was stirred with exclusion of moisture for 2 hr. For workup, the solvent was removed and the residue was taken up in $CH_2Cl_2$. It was washed with $H_2O$ and the aqueous phase was extracted once more with $CH_2Cl_2$. The combined organic phases were washed with saturated $NaHCO_3$ solution and dried with $MgSO_4$. Chromatography on silica gel (ethyl acetate/n-heptane 1:1→4:1) provided the product ester as a colorless solid. Melting point: 116° C.; MS(ES+): 427/429.

n-Butyl 2-methyl-4-{4-[1-(3α,7α,12α-trihydroxy-10β,13β-dimethyl-17β-(3carboxy-1-methylpropyl)hexadecahydrocyclopenta[a]phenanthren-3-yl)ethyn-2-yl]benzylamino}quinoline-3-carboxylate was prepared by the general process indicated (see Example 1). Melting point: 70° C.; MS(FAB): 779.

EXAMPLE 8

Isopropyl 2-methyl-4-{4-[1-(3α,7α, 12α-trihydroxy-10β,13β-dimethyl-17β-(3-carboxy-1-methylpropyl)hexadecahydrocyclopenta[a]phenanthren-3-yl)ethyn-2-yl]benzylamino}quinoline-3-carboxylate

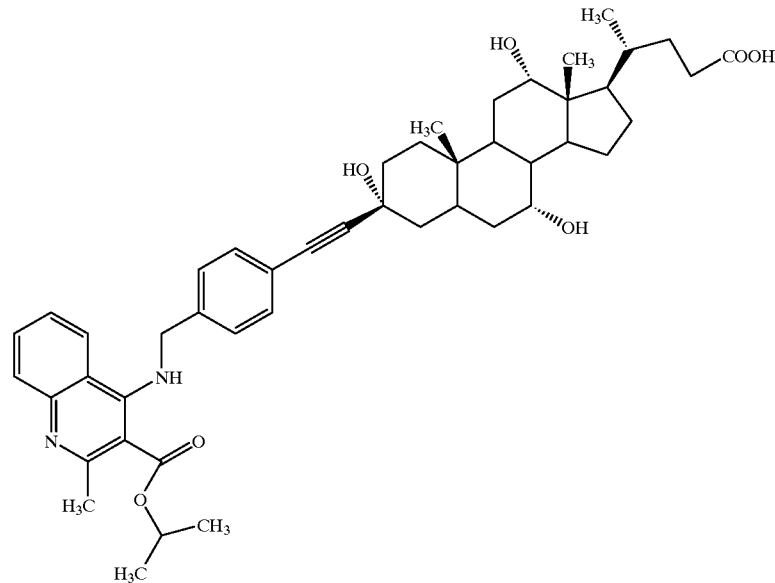

Preparation of Intermediates:

Intermediate 1: 3β-Ethynylcholic Acid

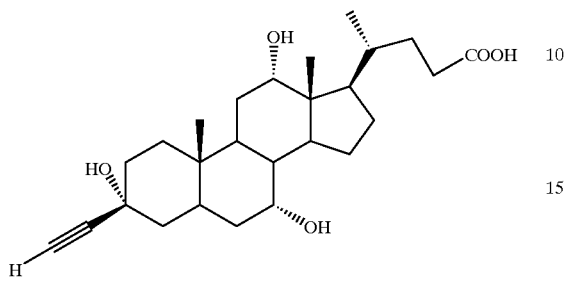

see Example 1

Intermediate 2: Isopropyl 4-(4-bromobenzylamino)-2-methylquinoline-3-carboxylate

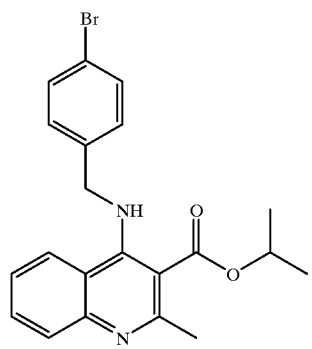

Synthetic Route:

a) Isopropyl 4-(4-bromobenzylamino)-2-methylquinoline-3-carboxylate was prepared in analogy to n-butyl 4-(4-bromobenzylamino)-2-methylquinoline-3-carboxylate (see Example 6) by transesterification of the corresponding methyl ester in an isopropanol/THF mixture, resulting in the title compound as a colorless oil. MS(ES+): 413/415.

Isopropyl 2-methyl-4-{4-[1-(3α,7α,12α-trihydroxy-10β,13β-dimethyl-17β-(3-carboxy-1-methylpropyl)hexadecahydrocyclopenta[a]phenanthren-3-yl)ethyn-2-yl]benzylamino}quinoline-3-carboxylate was prepared by the general process indicated (see Example 1). Melting point: 150° C.; MS(FAB): 765.

EXAMPLE 9

Methyl 2-methyl-4-benzylamino-6-{2-[3α,7α,12α-trihydroxy-10β,13β-dimethyl-17β-(3-carboxy-1-methylpropyl)hexadecahydrocyclopenta[a]-phenanthren-3-yl]ethyn-1-yl}quinoline-3-carboxylate

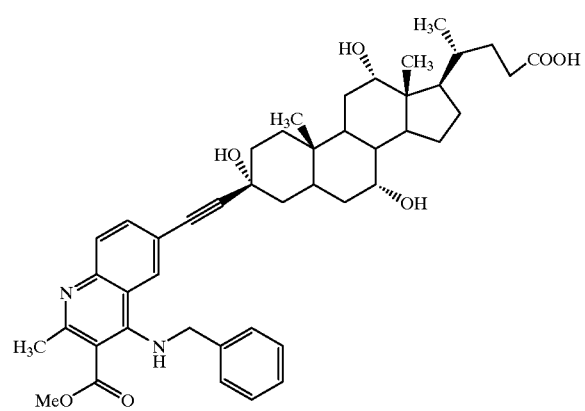

Preparation of Intermediates: Intermediate 1: 3β-Ethynylcholic Acid

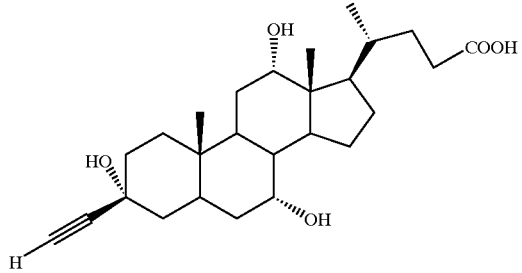

see Example 1

Intermediate 2: Methyl 4-(4-bromobenzylamino)-2-methylquinoline-3-carboxylate

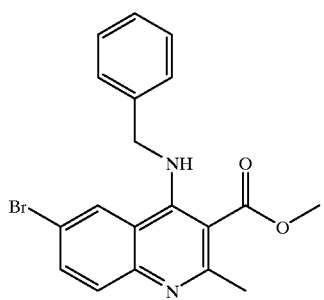

Synthetic Route:

a) 5-Bromo-2-aminobenzonitrile was prepared in a manner known from the literature (*Synlett.*, 450, 1994); MS(Cl): 197/199.

b) Methyl 6-bromo-4-amino-2-methylquinoline-3-carboxylate was prepared in a manner known to the skilled worker (Tetrahedron 51:12277 (1995)).

c) Methyl 6-bromo-4-benzylamino-2-methylquinoline-3-carboxylate was synthesized by the same process as described for 1-(4-(4-bromobenzylamino)-2-methylquinolin-3-yl)ethanone (Example 1, Intermediate 2c) starting from methyl 6-bromo4-amino-2-methylquinoline-3-carboxylate and 4-bromobenzyl bromide. Melting point: 89° C.; MS(ES+): 385/387.

Methyl 2-methyl-4-benzylamino-6-{2-[3α,7α,12α-trihydroxy-10β,13β-dimethyl-17β-(3-carboxy-1-methylpropyl)hexadecahydrocyclopenta[a]-phenanthren-3-yl]ethyn-1-yl}quinoline-3-carboxylate was prepared by the general process indicated (see Example 1). Melting point: 223° C. (decomposition); MS(ES+): 737.

EXAMPLE 10

Methyl 2-methyl-4-benzylamino-6-{2-[3α,7α,12α-trihydroxy-10β,13β-dimethyl-17β-(3-carboxy-1-methylpropyl)hexadecahydrocyclopenta[a] phenanthren-3-yl]eth-1-yl}quinoline-3-carboxylate

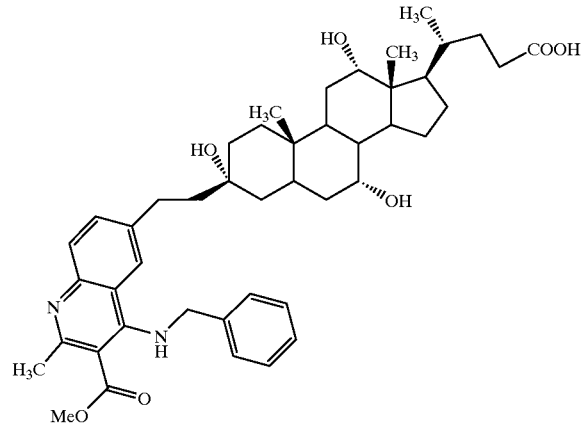

The product described in Example 8 was hydrogenated analogously to the method indicated in Example 2, resulting in the target compound as a pale yellow solid. Melting point: >185° C. (decomposition); MS(FAB): 741.

EXAMPLE 11

Methyl 2,5-dimethyl-4-{4-[1-(3α,7α,12α-trihydroxy-10β,13β-dimethyl-17β-(3-carboxy-1-methylpropyl)hexadecahydrocyclopenta[a] phenanthren-3-yl)ethyn-2-yl] benzylamino}quinoline-3-carboxylate

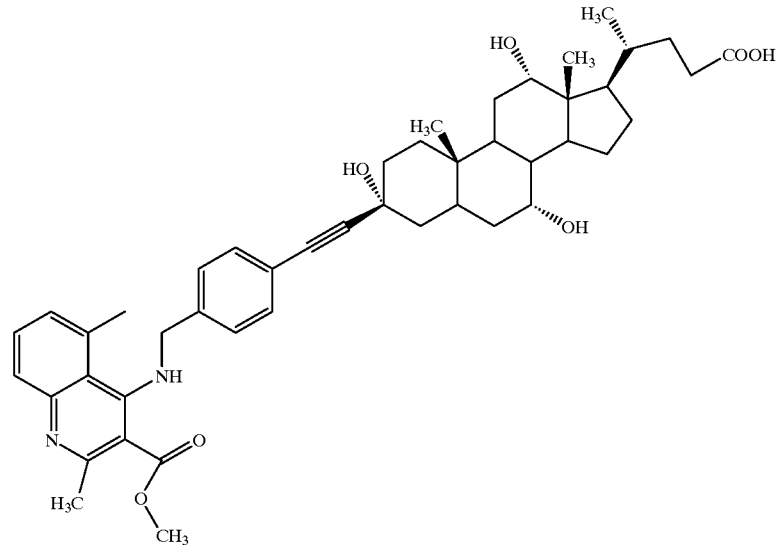

Preparation of Intermediates:

Intermediate 1: 3β-Ethynylcholic Acid

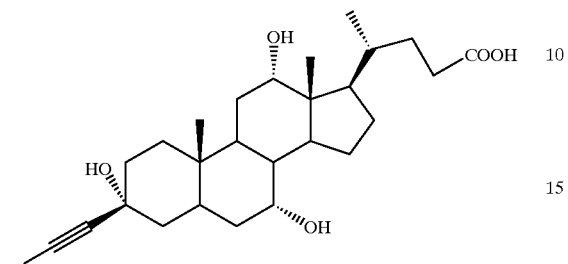

see Example 1

Intermediate 2: Methyl 4-(4-bromobenzylamino)-2,5-dimethylquinoline-3-carboxylate Synthetic Route:
a) Methyl 4-amino-2,5-dimethylquinoline-3-carboxylate was prepared analogously to Intermediate 2a, Example 6, in a manner known to the skilled worker (*Tetrahedron* 51:12277 (1995)).
b) Methyl 4-(4-bromobenzylamino)-2,5-dimethylquinoline-3-carboxylate was synthesized by the same process as described for 1-(4-(4-bromobenzylamino)-2-methylquinolin-3-yl)ethanone (Example 1, Intermediate 2c) starting from methyl 4-amino-2,5-dimethylquinoline-3-carboxylate and 4-bromobenzyl bromide. Melting point: 150° C.; MS(Cl+): 399/401.

Methyl 2,5-dimethyl-4-{4-[1-(3α,7α,12α-trihydroxy-10β,13β-dimethyl-17β-(3-carboxy-1-methylpropyl)hexadecahydrocyclopenta[a]phenanthren-3-yl)ethyn-2-yl]benzylamino}quinoline-3-carboxylate was prepared by the general process indicated (see Example 1). Melting point: >155° C.; MS(ES+): M⁺+H=751.

EXAMPLE 12

Methyl 2,5-dimethyl-4-{4-[1-(3α,7α,12α-trihydroxy-10β,13β-dimethyl-17β-(3-carboxy-1-methylpropyl)hexadecahydrocyclopenta[a]phenanthren-3-yl)eth-2-yl]benzylamino}quinoline-3-carboxylate

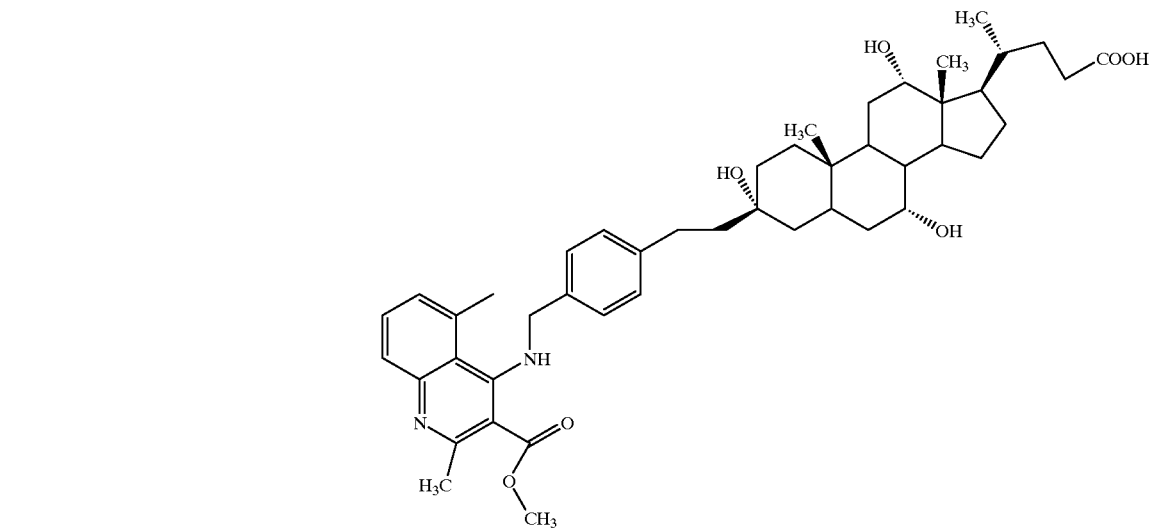

The product described in Example 11 was hydrogenated analogously to the method indicated in Example 2, resulting in the target compound as a pale yellow solid. Melting point: >180° C. decomposition; MS(ES+): M⁺+H=756.

EXAMPLE 13

2-Methyl-3-acetyl-4-{3-[1-(3α,7α,12α-trihydroxy-10β,13β-dimethyl-17β-(3-carboxy-1-methylpropyl)hexadecahydrocyclopenta[a]phenanthren-3-yl)ethyn-2-yl]benzylamino}quinoline

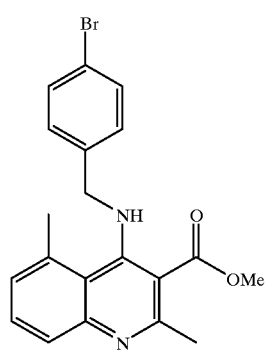

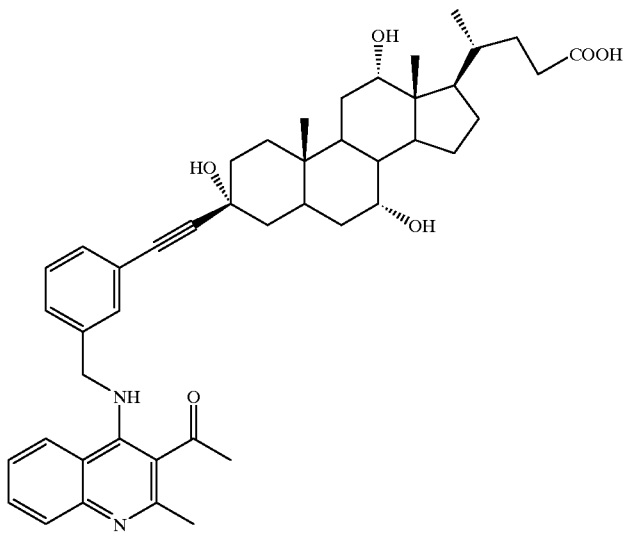

Preparation of Intermediates:
Intermediate 1: 3β-Ethynylcholic Acid

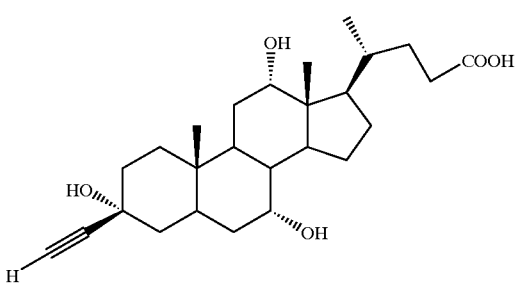

see Example 1
Intermediate 2: 1-(4-(3-Bromobenzylamino)-2-methylquinolin-3-yl)ethanone

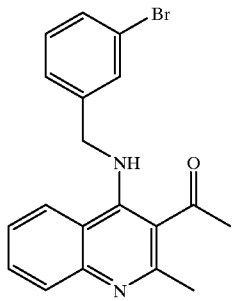

Synthetic Route:
a) 1-(4-Amino-2-methylquinolin-3-yl)ethanone was prepared analogously to Intermediate 2a, Example 6, by tin tetrachloride-promoted reaction of 2-aminobenzonitrile and acetyl acetone in a manner known from the literature (*Tetrahedron* 51:12277 (1995)).
b) 1-(4-(3-Bromobenzylamino)-2-methylquinolin-3-yl)ethanone was synthesized by the same process as described for 1-(4-(4-bromo-benzylamino)-2-methylquinolin-3-yl)ethanone (Example 1, Intermediate 2c) starting from 1-(4-amino-2-methylquinolin-3-yl)ethanone and 3-bromobenzyl bromide. Melting point: 109° C.; MS(ES+): 369/371.

2-Methyl-3-acetyl-4-{3-[1-(3α,7α,12α-trihydroxy-10β,13β-dimethyl-17β-(3-carboxy-1-methylpropyl) hexadecahydrocyclopenta[a]phenanthren-3-yl)ethyn-2-yl]benzyl}aminoquinoline was prepared by the general process indicated (see Example 1). Melting point: >195° C. decomposition; MS(ES+): M⁺+H=721.

EXAMPLE 14

2-Methyl-3-acetyl-4-{3-[1-(3α,7α,12α-trihydroxy-10β,13β-dimethyl-17β-(3-carboxy-1-methylpropyl) hexadecahydrocyclopenta[a]phenanthren-3-yl)eth-2-yl]benzylamino}quinoline

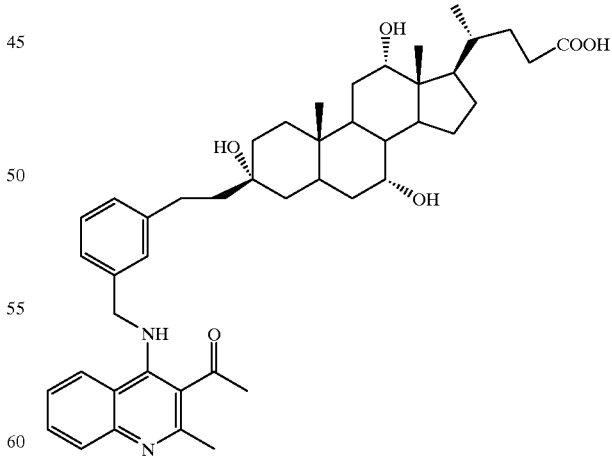

The title compound was obtained by catalytic hydrogenation, as described in Example 2, of the product described in Example 13. Melting point: >170° C. decomposition; MS(FAB+): M⁺=725.

EXAMPLE 15

2-Methyl-3-acetyl-4-{3-[1-(3α,7α,12α-trihydroxy-10β,13β-dimethyl-17β-(3-carboxymethylcarbamoyl-1-methylpropyl)hexadecahydrocyclopenta[a]phenanthren-3-yl)eth-2-yl]benzylamino}quinoline

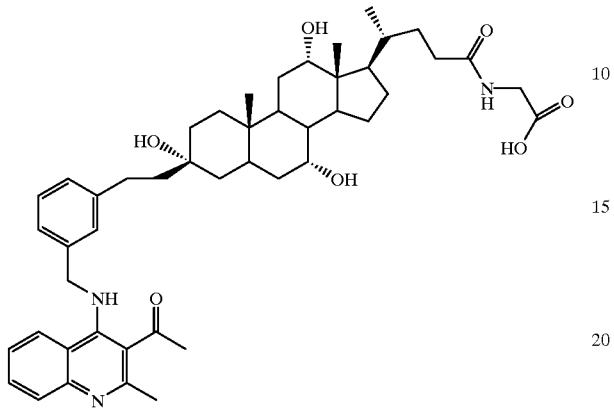

Synthetic Route:

a) 2-Methyl-3-acetyl-4-{3-[1-(3α,7α,12α-trihydroxy-10β,13β-dimethyl-17β-(3-ethoxycarbonylmethylcarbamoyl-1-methylpropyl)hexadecahydrocyclopenta[a]phenanthren-3-yl)eth-2-yl]benzylamino}quinoline. 55 mg of the product prepared in Example 14 were introduced into 5 ml of abs. DMF and, at 0° C., 1 ml of a solution of 0.1 ml of triethylamine in 10 ml of abs. DMF was added. Addition of 25 mg of TOTU was followed by stirring at 0° C. for 20 min and at room temperature for 30 min. This solution was added to a solution consisting of 11 mg of glycine ethyl ester hydrochloride in 2 ml of DMF, 2 ml of $H_2O$ and 1 ml of triethylamine and stirred at room temperature until the conversion was complete. The solvent was distilled off and the residue was chromatographed on silica gel, resulting in 41 mg of the corresponding ethyl ester.

b) 2-Methyl-3-acetyl-4-{3-[1-(3α,7α,12α-trihydroxy-10β,13β-dimethyl-17β-(3-carboxymethylcarbamoyl-1-methylpropyl)hexadecahydrocyclopenta[a]phenanthren-3-yl)eth-2-yl]benzylamino}quinoline. 41 mg of the prepared ethyl ester were dissolved in 5 ml of methanol and, at room temperature, a solution of 28 mg of KOH in 1.5 ml of $H_2O$ was added dropwise and stirred at room temperature. After 2 hours, the solvent was removed, and the residue was taken up in 5 ml of $H_2O$ and a pH of 5 was adjusted with dilute HCl, whereupon the required product precipitated. The precipitate was filtered off with suction and dried in air. MS(ES+): $M^+ + H$: 782.

EXAMPLE 16

2-Methyl-3-acetyl-4-{3-[1-(3α,7α,12α-trihydroxy-10β,13β-dimethyl-17β(3-(2-sulfoethylcarbamoyl)-1-methylpropyl)hexadecahydrocyclopenta[a]phenanthren-3-yl)eth-2-yl]benzylamino}quinoline

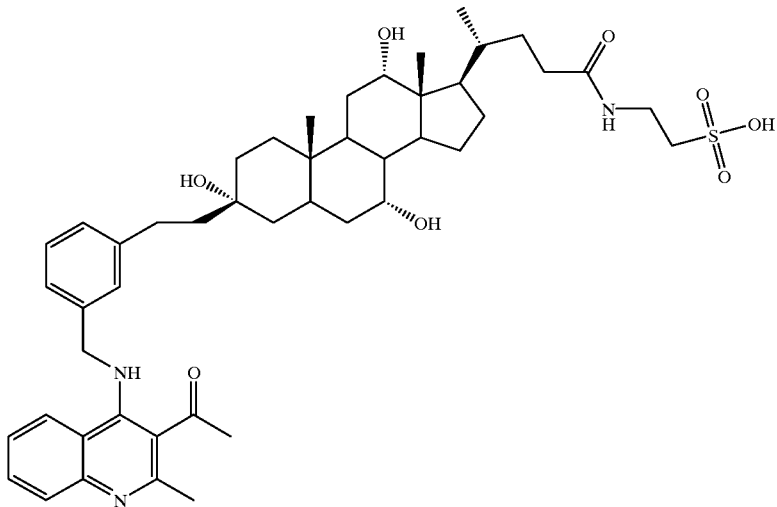

55 mg of the product prepared in Example 14 were introduced into 5 ml of abs. DMF and, at 0° C., 1 ml of a solution of 0.1 ml of triethylamine in 10 ml of abs. DMF was added. Addition of 25 mg of TOTU was followed by stirring at 0° C. for 20 min and at room temperature for 30 min. This solution was added to a solution consisting of 10 mg of taurine in 2 ml of DMF, 2 ml of $H_2O$ and 1 ml of triethylamine and stirred at room temperature until conversion was complete. The solvent was removed, and the residue was chromatographed on silica gel, resulting in 36 mg of the title compound in the form of a pale yellowish solid. MS(ES+): $M^++H$: 832.

EXAMPLE 17

2-Methyl-3-acetyl-4-{2-[1-(3α,7α,12α-trihydroxy-10β,13β-dimethyl-17β-(3-carboxy-1-methylpropyl)hexadecahydrocyclopenta[a]phenanthren-3-yl)ethyn-2-yl]benzylamino}quinoline

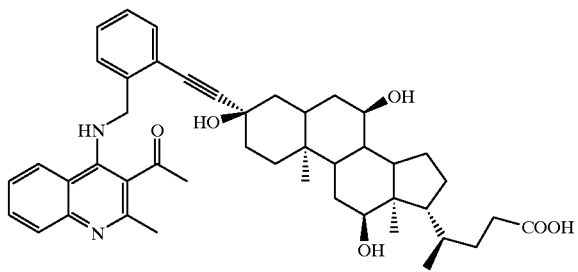

Preparation of Intermediates:
Intermediate 1: 3β-Ethynylcholic Acid

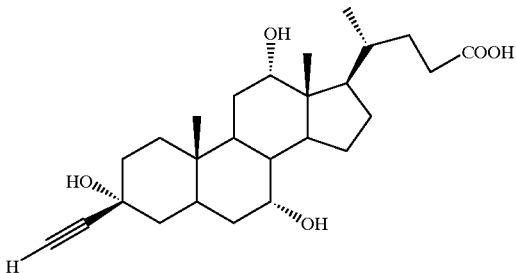

see Example 1
Intermediate 2: 1-(4-(3-Bromobenzylamino)-2-methylquinolin-3-yl)ethanone

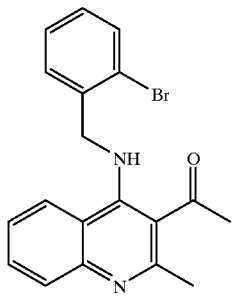

Synthetic Route:
a) 1-(4-Amino-2-methylquinolin-3-yl)ethanone: see Example 13 (Tetrahedron 51 (1995), 12277).
b) 4-(2-Bromobenzylamino)-2-methylquinolin-3-yl)ethanone was synthesized by the same process as described for 1-(4-(4-bromobenzylamino)-2-methylquinolin-3-yl)ethanone (Example 1, Intermediate 2c) starting from 1-(4-amino-2-methylquinolin-3-yl)ethanone and 2-bromobenzyl bromide. Melting point: 134° C.; MS(ES+): 369/371.

2-Methyl-3-acetyl-4-{2-[1-(3α,7α,12α-trihydroxy-10β,13β-dimethyl-17β-(3-carboxy-1-methylpropyl)hexadecahydrocyclopenta[a]phenanthren-3-yl)ethyn-2-yl]benzylamino}quinoline was prepared by the general process indicated (see Example 1) from the two intermediates. MS(ES+): $M^++H=721$.

EXAMPLE 18

2-Methyl-3-acetyl-4-{2-[1-(3α,7α,12α-trihydroxy-10β,13β-dimethyl-17β(3-carboxy-1-methylpropyl)hexadecahydrocyclopenta[a]phenanthren-3-yl)eth-2-yl]benzylamino}quinoline

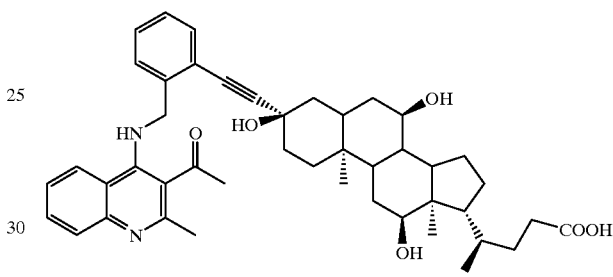

Hydrogenation of the product compound from Example 17 by the method stated in Example 2 provided the required product in the form of a pale yellowish solid. Melting point: >165° C. decomposition; MS(ES+): 725.

EXAMPLE 19

Methyl 4-[3β-(2-{4-[(3-acetyl-2-methylquinolin4-ylamino)methyl]benzoylamino)ethoxy)-7α,12α-dihydroxy-10β,13β-dimethylhexadecahydrocyclopenta[a]phenanthren-17β-yl]pentanoate

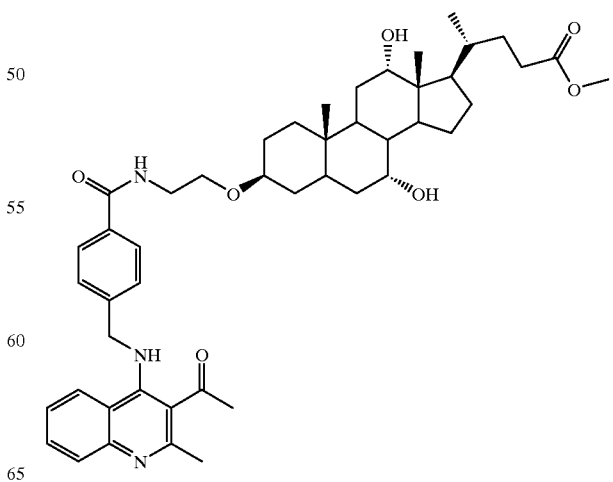

Preparation of Intermediates:

Intermediate 1: Methyl 3β-(2-aminoethoxy)cholate

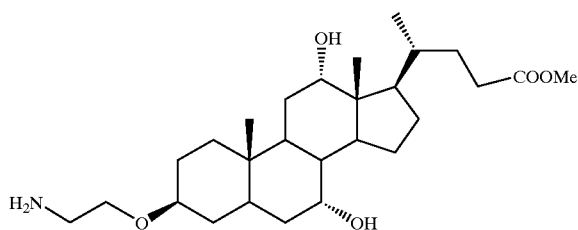

see Example 3 (*Tetrahedron Lett.*, 33:195 (1992); *Tetrahedron Lett.*, 34:817 (1993)).

Intermediate 2: 4-[(3-Acetyl-2-methylquinolin-4-yamino) methyl]benzoic Acid

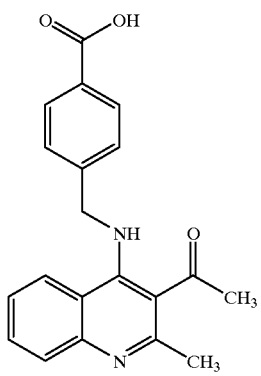

Synthetic Route:

a) The synthesis of 2-methyl-3-acetyl-4-(4-bromobenzylamino)quinoline was described in Example 1 for Intermediate 2.

b) 4-[(3-Acetyl-2-methylquinolin-4-ylamino)methyl] benzoic acid.

370 mg of 2-methyl-3-acetyl-4-(4-bromobenzylamino) quinoline, 79 mg of triphenylphosphine and 78 mg of calcium formate were dissolved in 4 ml of DMF and 4 ml of benzene. Under protective gas, 9 mg of palladium acetate were added and the solution was heated to 120° C. under a CO atmosphere. After two hours, 58 mg of tetrakistriphenylphosphine palladium were added and stirring at 120° C. was continued. Stirring was continued at the stated temperature until no further increase in conversion was detected. If necessary, additional palladium catalyst was added. For workup, 2N NaOH was added and the mixture was extracted with dichloromethane. The organic phase was extracted once again with 2N NaOH, and the combined aqueous phases were extracted with dichloromethane. The NaOH extracts were adjusted to a pH of 6 with 6N HCl and concentrated in vacuo. The residue was taken up in a little methanol, and insoluble salts were filtered off. The filtrate was concentrated and taken up in a little H₂O. The resulting product was a yellow insoluble solid, which was filtered off with suction and dried in air. 81 mg of a yellow solid were obtained. Melting point: >210° C. decomposition; MS(ES+): 335.

Methyl 4-[3β-(2-{4-[(3-acetyl-2-methylquinolin-4-ylamino)methyl]benzoylamino)ethoxy)-7α,12α-dihydroxy-10β,13β-dimethylhexadecahydrocyclopenta[a]phenanthren-17β-yl]-pentanoate 67 mg of Intermediate 2 were dissolved in 5 ml of DMF and, at 0° C., 1 ml of a solution of 0.28 ml of triethylamine in 10 ml of DMF was added. Addition of a solution of 66 mg of TOTU in 2 ml of DMF was followed by stirring at 0° C. for 30 min and at room temp. for a further 45 min. This solution was added dropwise to a second solution of 93 mg of Intermediate 1 in 2 ml of DMF and 1 ml of triethylamine and was stirred at room temp. until conversion was found to be complete. For workup, the residue after concentration in vacuo was taken up in ethyl acetate. The precipitate was filtered off and the filtrate was washed with a NaHCO₃ solution and with H₂O. The organic phase was separated off and dried with MgSO₄, and the solvent was removed. The residue obtained was chromatographed together with the removed precipitate on silica gel, resulting in 71 mg of the product as a yellow-orange solid. Melting point: >98° C. decomposition; MS(ES+): 782.

EXAMPLE 20

4-[3β-(2-{4-[(3-Acetyl-2-methylquinolin-4-ylamino) methyl]benzoylamino)-ethoxy)-7α,12α-dihydroxy-10β,13β-dimethylhexadecahydrocyclopenta[a] phenanthren-17β-yl]pentanoic acid.

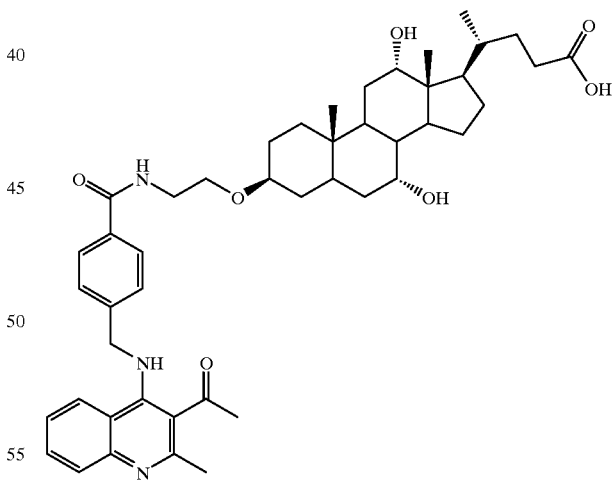

The ester obtained in Example 19 was reacted analogously to the hydrolysis described in Example 4, resulting in the required product as a colorless solid. Melting point: >145° C. decomposition; MS(ES+): 768.

EXAMPLE 21

Methyl 2-ethyl4-{4-[1-(3α,7α,12α-trihydroxy-10β, 13β-dimethyl-17β-(3-carboxy-1-methylpropyl) hexadecahydrocyclopenta[a]phenanthren-3-yl)ethyn-2-yl]benzylamino}quinoline-3-carboxylate

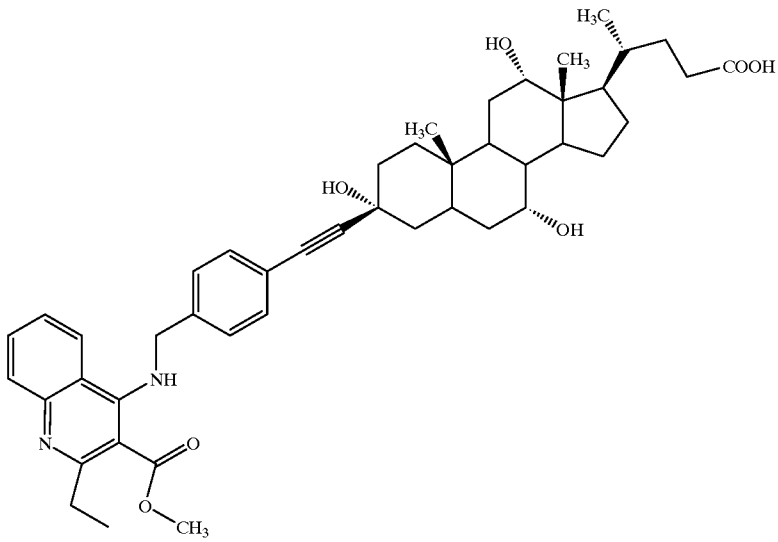

Preparation of Intermediates:

Intermediate 1: 3β-Ethynylcholic Acid

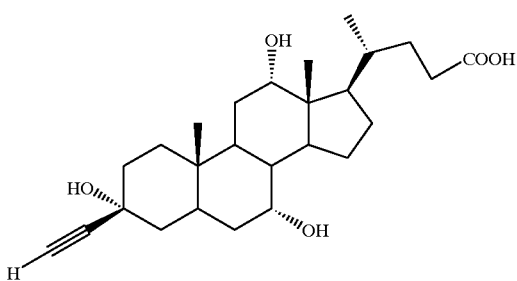

see Example 1

Intermediate 2: Methyl 4-(4-bromobenzylamino)-2-ethylquinoline-3-carboxylate

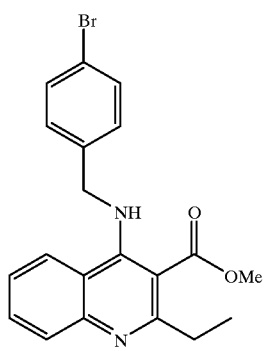

Synthetic Route:

a) Methyl 4-amino-2-ethylquinoline-3-carboxylate was prepared in a manner known to the skilled worker (*Tetrahedron* 51:12277 (1995)).

b) Methyl 4-(4-bromobenzylamino)-2-ethylquinoline-3-carboxylate was synthesized by the same process as described for 1-(4-(4-bromobenzylamino)-2-methylquinolin-3-yl)ethanone (Example 1, Intermediate 2c) starting from methyl 4-amino-2-ethylquinoline-3-carboxylate and 4-bromobenzyl bromide. MS(ES+): 399/401.

Methyl 2-ethyl-4-{4-[1-(3α,7α,12α-trihydroxy-10β,13β-dimethyl-17β-(3-carboxy-1-methylpropyl)hexadecahydrocyclopenta[a]phenanthren-3-yl)ethyn-2-yl]benzylamino}quinoline-3-carboxylate was prepared by the general process indicated (see Example 1). Melting point: >200° C.; MS(FAB): 751.

EXAMPLE 22

Methyl-2-ethyl-4-{4-[1-(3α,7α,12α-trihydroxy-10β, 13β-dimethyl-17β-(3-carboxy-1-methylpropyl) hexadecahydrocyclopenta[a]phenanthren-3-yl)eth-2-yl]benzylamino}quinoline-3-carboxylate

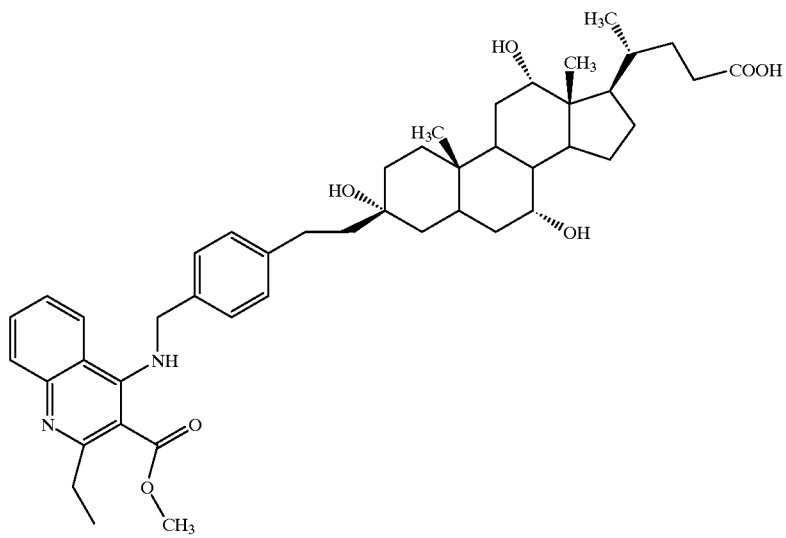
The product described in Example 21 was hydrogenated analogously to the method indicated in Example 2, resulting in the target compound as a pale yellow solid. Melting point: >190° C. (decomposition); MS(ES+): 755.
EXAMPLE 23
2-Methyl-3-acetyl-4-{4-[1-(3α,7α,12α-trihydroxy-10β,13β-dimethyl-17β-(3-carboxy-1-methylpropyl) hexadecahydrocyclopenta[a]phenanthren-3-yl)ethyn-2-yl]-3-fluorobenzylamino}quinoline
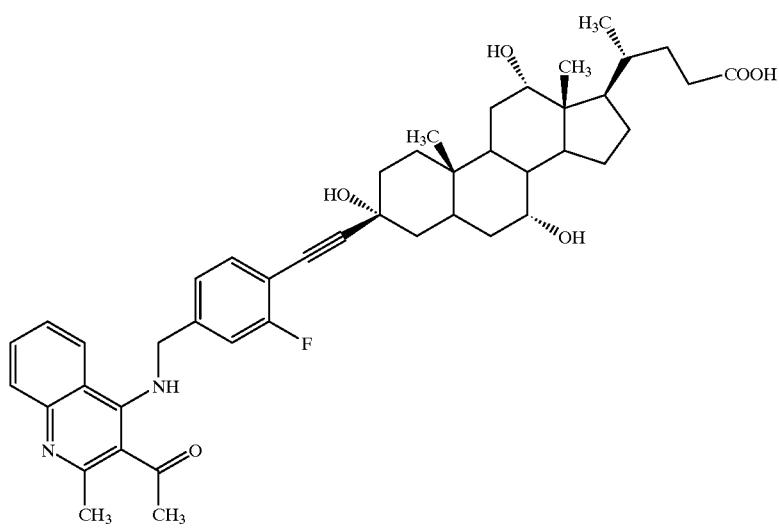

Preparation of Intermediates:
Intermediate 1: 3β-Ethynylcholic Acid

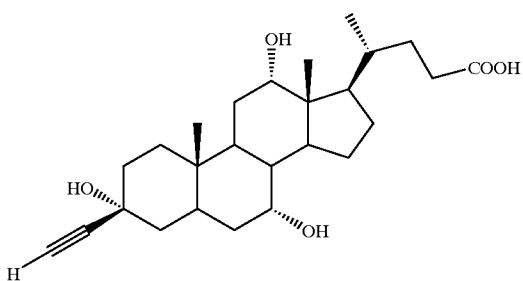

see Example 1
Intermediate 2: 1-(4-(4-Bromo-3-fluorobenzylamino)-2-methylquinolin-3-yl)ethanone

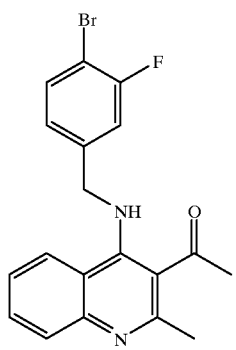

Synthetic Route:

a) 1-(4-Amino-2-methylquinolin-3-yl)ethanone; see Example 13 (*Tetrahedron* 51:12277 (1995)).

b) 1-(4-(4-Bromo-3-fluorobenzylamino)-2-methylquinolin-3-yl)ethanone was synthesized by the same process as described for 1-(4-(4-bromobenzylamino)-2-methylquinolin-3-yl)ethanone (Example 1, Intermediate 2c) starting from 1-(4-amino-2-methylquinolin-3-yl)ethanone and 4-bromo-3-fluorobenzyl bromide. MS(ES+): 387/389.

2-Methyl-3-acetyl-4-{4-[1-(3α,7α,12α-trihydroxy-10β,13β-dimethyl-17β-(3-carboxy-1-methylpropyl)hexadecahydrocyclopenta[a]phenanthren-3-yl)ethyn-2-yl]-3-fluorobenzylamino}quinoline was prepared by the general process indicated (see Example 1). MS(FAB): 739.

EXAMPLE 24

2-Methyl-3-acetyl-4-{4-[1-(3α,7α,12α-trihydroxy-10β,13β-dimehtyl-17β-(3-carboxy-1-methylpropyl)hexadecahydrocyclopenta[a]phenanthren-3-yl)eth-2-yl]-3-fluorobenzylamino}quinoline

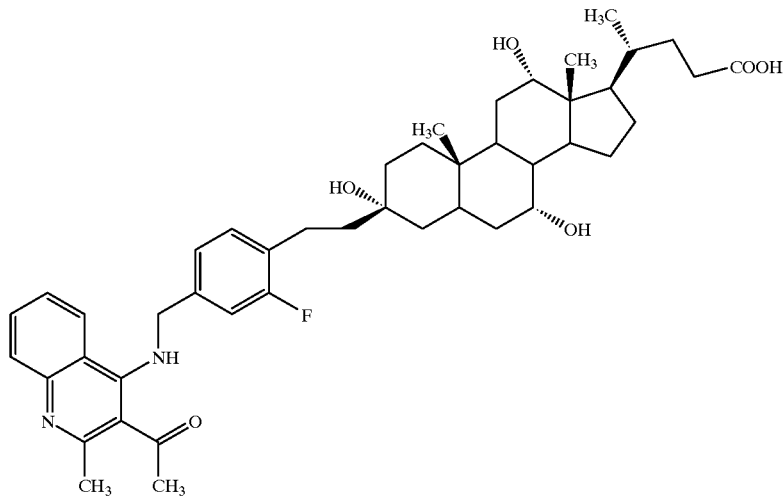

The product described in Example 23 was hydrogenated analogously to the method indicated in Example 2, resulting in the target compound as a pale yellow solid. MS(ES+): 744.

EXAMPLE 25

2-Methyl-3-acetyl-4-{4-[1-(3α,7α,12α-trihydroxy-10β,13β-dimethyl-17β-(3-carboxy-1-methylpropyl)hexadecahydrocyclopenta[a]phenanthren-3-yl)ethyn-2-yl]-3-chlorobenzylamino}quinoline

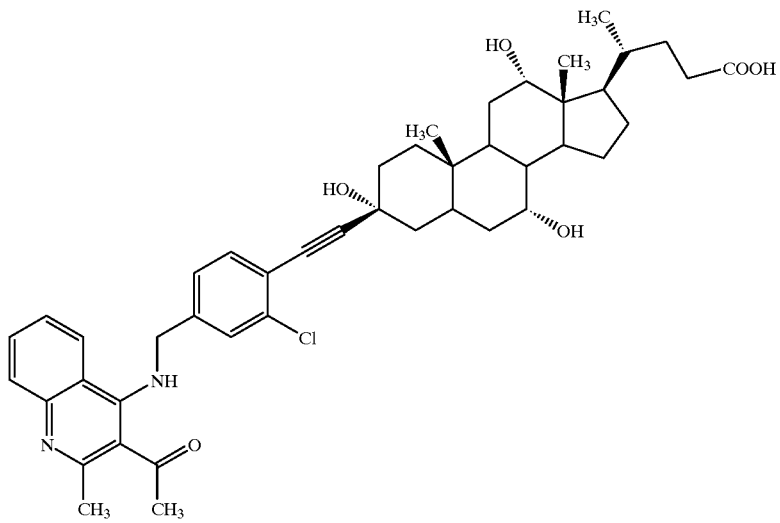

Preparation of Intermediates:

Intermediate 1: 3β-Ethynylcholic Acid

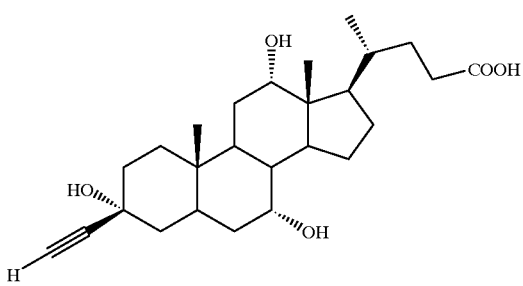

see Example 1

Intermediate 2: 1-(4-(4-Bromo-3-chlorobenzylamino)-2-methylquinolin-3-yl)ethanone

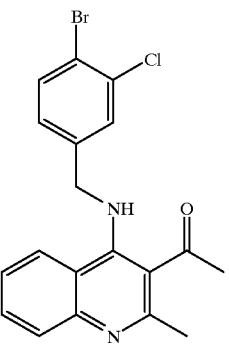

Synthetic Route:

a) 1-(4-Amino-2-methylquinolin-3-yl)ethanone; see Example 13 (*Tetrahedron* 51:12277 (1995)).

b) 1-(4-(4-Bromo-3-chlorobenzylamino)-2-methylquinolin-3-yl)ethanone was synthesized by the same process as described for 1-(4-(4-bromobenzylamino)-2-methylquinolin-3-yl)ethanone (Example 1, Intermediate 2c) starting from 1-(4-amino-2-methylquinolin-3-yl)ethanone and 4-bromo-3-chlorobenzyl bromide. MS(ES+):403/405.

2-Methyl-3-acetyl-4-{4-[1-(3α,7α,12α-trihydroxy-10β,13β-dimethyl-17β-(3-carboxy-1-methylpropyl)hexadecahydrocyclopenta[a]phenanthren-3-yl)ethyn-2-yl]-3-chlorobenzylamino}quinoline was prepared by the general process indicated (see Example 1). MS(FAB): 755.

EXAMPLE 26

2-Methyl-3-acetyl-4-4-[1-(3α,7α,12α-trihydroxy-10β,13β-dimethyl-17β-(3-carboxy-1-methylpropyl)hexadecahydrocyclopenta[a]phenanthren-3-yl)ethyn-2-yl]-2-fluorobenzylamino}quinoline

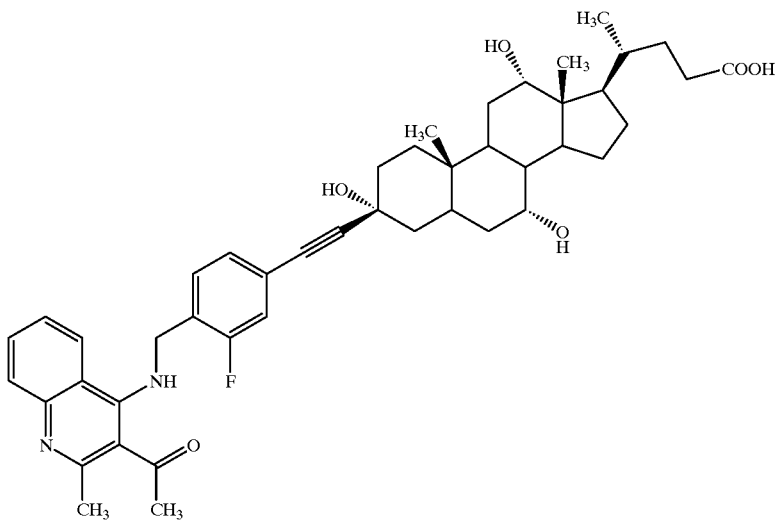

Preparation of Intermediates:
Intermediate 1: 3β-Ethynylcholic Acid

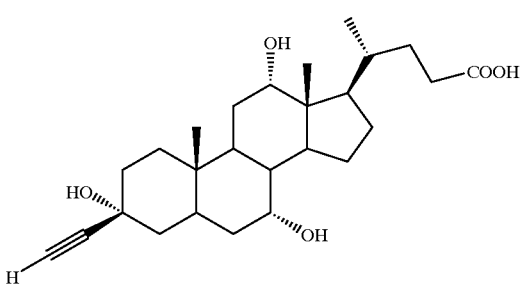

see Example 1

Intermediate 2: 1-(4-(4-Bromo-2-fluorobenzylamino)-2-methylquinolin-3-yl)ethanone

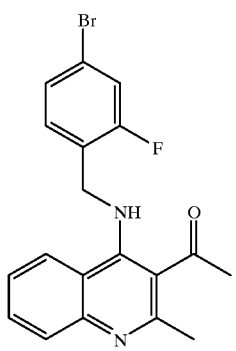

Synthetic Route:

a) 1-(4-Amino-2-methylquinolin-3-yl)ethanone; see Example 13 (*Tetrahedron* 51: 12277 (1995)).

b) 1-(4-(4-Bromo-2-fluorobenzylamino)-2-methylquinolin-3-yl)ethanone was synthesized by the same process as described for 1-(4-(4-bromobenzylamino)-2-methylquinolin-3-yl)ethanone (Example 1, Intermediate 2c) starting from 1-(4-amino-2-methylquinolin-3-yl)ethanone and 4-bromo-2-fluorobenzyl bromide. MS(ES+): 387/389.

2-Methyl-3-acetyl-4-{4-[1-(3α,7α,12α-trihydroxy-10β,13β-dimethyl-17β-(3-carboxy-1-methylpropyl)hexadecahydrocyclopenta[a]phenanthren-3-yl)ethyn-2-yl]-2-fluorobenzylamino}quinoline was prepared by the general process indicated (see Example 1). MS(ES+): 739.

EXAMPLE 27

2-Methyl-3-acetyl-4-{4-[1-(3α,7α,12α-trihydroxy-10β,13β-dimethyl-17β-(3-carboxy-1-methylpropyl)hexadecahydrocyclopenta[a]phenanthren-3-yl)eth-2-yl]-2-fluorobenzylamino}quinoline

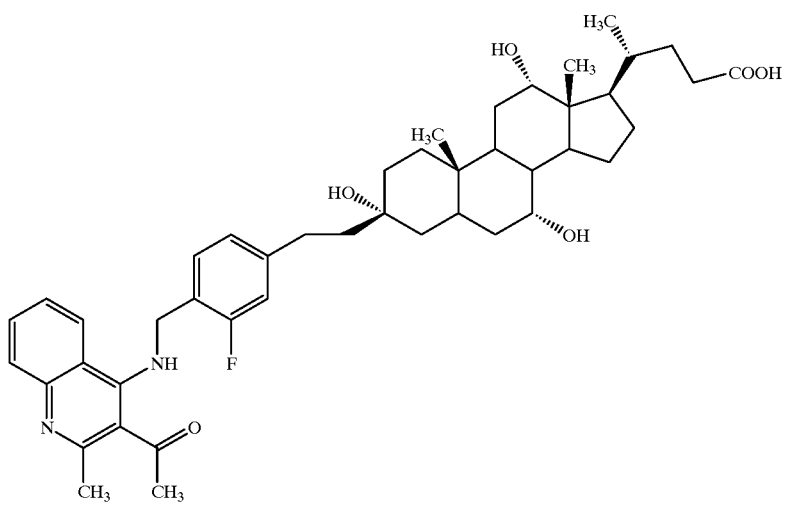
The product described in Example 26 was hydrogenated analogously to the method indicated in Example 2, resulting in the target compound as a pale yellow solid. MS(ES+): 744.
EXAMPLE 28
2-Methyl-3-acetyl-4-{4-[1-(3α,7α,12α-trihydroxy-10β,13β-dimethyl-17β-(3-carboxy-1-methylpropyl) hexadecahydrocyclopenta[a]phenanthren-3-yl)ethyn-2-yl]-2-chlorobenzylamino}quinoline
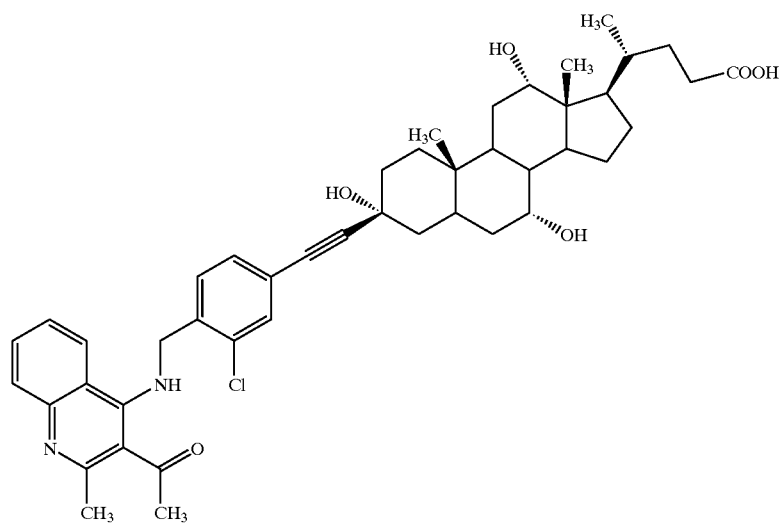

Preparation of Intermediates:
   Intermediate 1: 3β-Ethynylcholic Acid

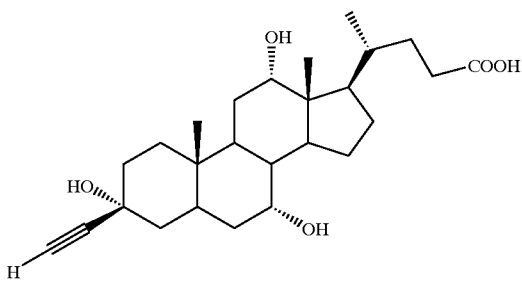

see Example 1

Intermediate 2: 1-(4-(4-Bromo-2-chlorobenzylamino)-2-methylquinolin-3-yl)ethanone

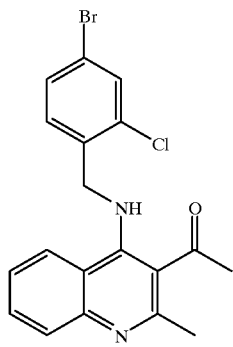

Synthetic Route:

a) 1-(4-Amino-2-methylquinolin-3-yl)ethanone; see Example 13 (*Tetrahedron* 51: 12277 (1995)).

b) 1-(4-(4-Bromo-2-chlorobenzylamino)-2-methylquinolin-3-yl)ethanone was synthesized by the same process as described for 1-(4-(4-bromobenzylamino)-2-methylquinolin-3-yl)ethanone (Example 1, Intermediate 2c) starting from 1-(4-amino-2-methylquinolin-3-yl)ethanone and 4-bromo-2-chlorobenzyl bromide. MS(FAB+): 403/405.

2-Methyl-3-acetyl-4-{4-[1-(3α,7α,12α-trihydroxy-10β,13β-dimethyl-17β-(3-carboxy-1-methylpropyl)hexadecahydrocyclopenta[a]phenanthren-3-yl)ethyn-2-yl]-2-chlorobenzylamino}quinoline was prepared by the general process indicated (see Example 1). MS(FAB+): 756.

EXAMPLE 29

2-Methyl-3-acetyl-4-{4-[1-(3α,7α,12α-trihydroxy-10β,13β-dimethyl-17β(3-carboxy-1-methylpropyl)hexadecahydrocyclopenta[a]phenanthren-3-yl)eth-2-yl]-2-chlorobenzylamino}quinoline

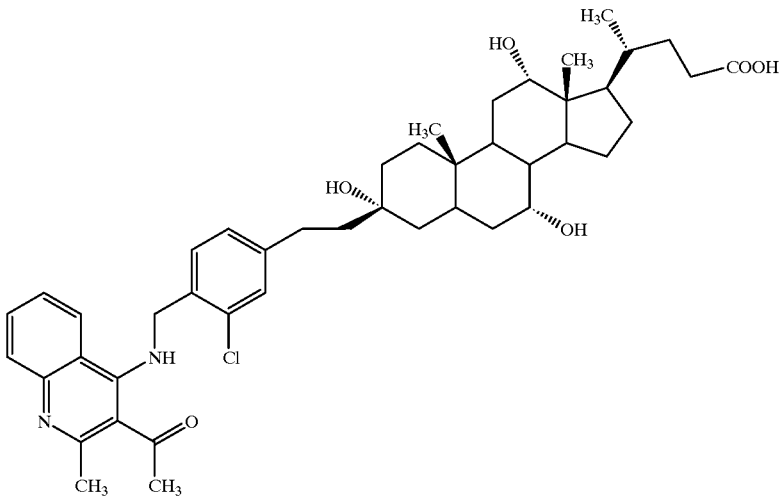

The product described in Example 28 was hydrogenated analogously to the method indicated in Example 2, resulting in the target compound as a pale yellow solid. MS(ES+): 760.

EXAMPLE 30

2,6-Dimethyl-3-acetyl-4-{4-[1-(3α,7α,12α-trihydroxy-10β,13β-dimethyl-17β-(3-carboxy-1-methylpropyl)hexadecahydrocyclopenta[a]phenanthren-3-yl)ethyn-2-yl]benzylamino}pyridine.

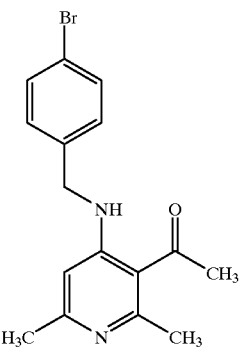

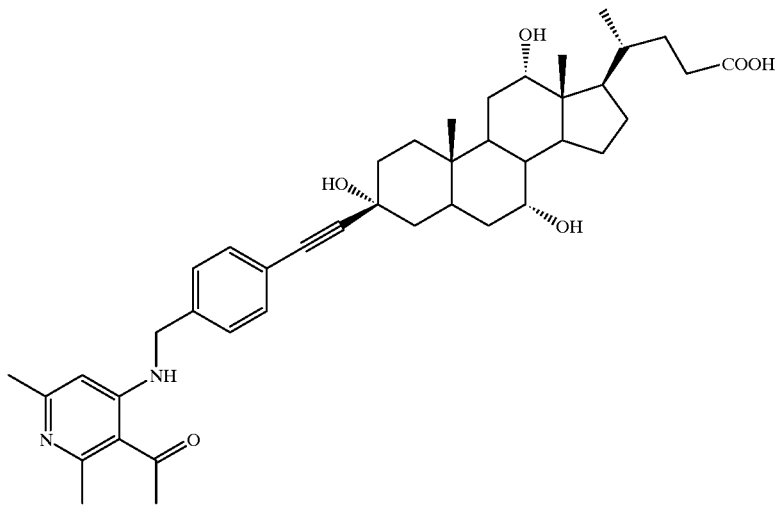

Preparation of Intermediates:

Intermediate 1: 3β-Ethynylcholic Acid

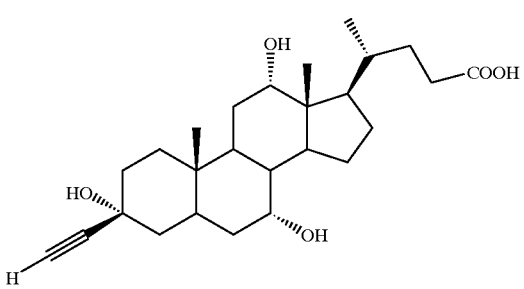

see Example 1.

Intermediate 2: 1-[4-(4-Bromobenzylamino)-2,6-dimethylpyridin-3-yl]ethanone

Synthetic Route:

a) 3-Acetyl-2,6-dimethyl-1H-pyridin-4-one was prepared by a previously published process (*Chem. Pharm. Bull.*, 31:4303 (1983)).

b) 1-(4-Chloro-2,6-dimethylpyridin-3-yl)ethanone was synthesized in a manner known to the skilled worker (*J. Heterocyclic Chem.*, 18:603 (1981)).

c) 1-[4-(4-Bromobenzylamino)-2,6-dimethylpyridin-3-yl]ethanone g of 1-(4-chloro-2,6-dimethylpyridin-3-yl)ethanone was dissolved in 10 ml of dimethylacetamide, and 1.5 equivalents of 4-bromobenzylamine were added. The solution was heated at 140 to 150° C. until no further increase in conversion was detected. If necessary, a further equivalent of 4-bromobenzylamine was added. For workup, the solvent was distilled off in vacuo, and the residue was chromatographed on silica gel, resulting in the title compound as a yellow oil. MS(ES+): 333/335.

2,6-Dimethyl-3-acetyl-4-{4-[1-(3α,7α,12α-trihydroxy-10β,13β-dimethyl-17β-(3-carboxy-1-methylpropyl)hexadecahydrocyclopenta[a]phenanthren-3-yl)ethyn-2-yl]benzylamino}pyridine was prepared by the general process (see Example 1). MS(ES+): 685.

EXAMPLE 31

2,6-Dimethyl-3-acetyl-4-{4-[1-(3α,7α,12α-trihydroxy-10β,13β-dimethyl-17β-(3-carboxy-1-methylpropyl)hexadecahydrocyclopenta[a]phenanthren-3-yl)eth-2-yl]benzylamino}pyridine.

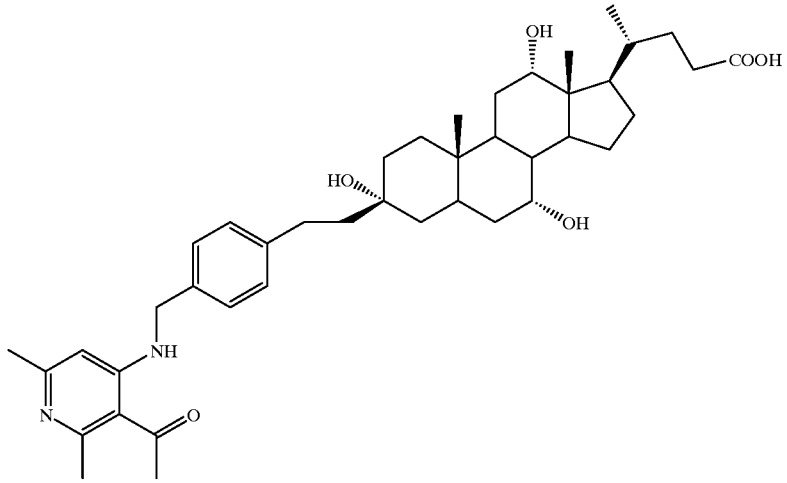

The product obtained in Example 30 was hydrogenated by the process described in Example 2, resulting in the title compound as a pale yellowish solid. MS(ES+); 689.

EXAMPLE 32

2-Ethyl-6-methyl-5-acetyl-4-{4-[1-(3α,7α,12α-trihydroxy-10β,13β-dimethyl-17β-(3-carboxy-1-methylpropyl)hexadecahydrocyclopenta[a]phenanthren-3-yl)ethyn-2-yl]benzylamino}pyridine.

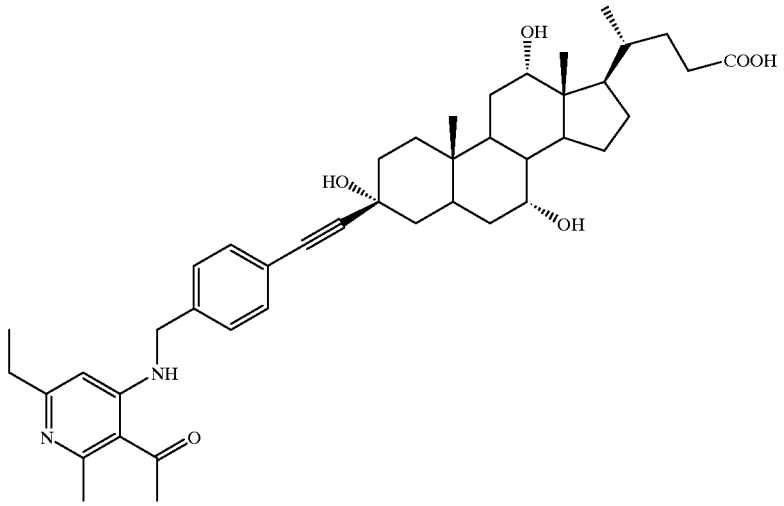

Preparation of Intermediates:

Intermediate 1: 3β-Ethynylcholic Acid

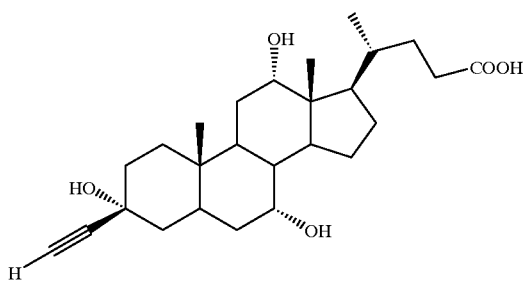

see Example 1.

Intermediate 2: 1-[4-(4-Bromobenzylamino)-2-ethyl-6-methylpyridin-5-yl]ethanone

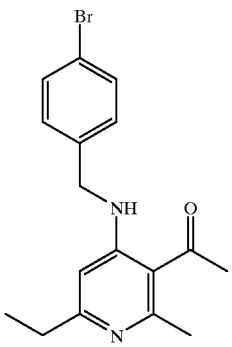

Synthetic Route:

a) 2,2-Dimethyl-5-propionyl-[1,3]dioxane4,6-dione was synthesized in a manner known from the literature (*J. Org. Chem.*, 43:2087 (1978)).

b) 3-Acetyl-6-ethyl-2-methyl-1H-pyridin4-one was synthesized by a method based on that described in Example 30 (Example 30; Intermediate 2a) (*Chem. Pharm. Bull.*, 31:4303 (1983)).

c) 1-(4-Chloro-6-ethyl-2-methylpyridin-3-yl)ethanone was prepared in analogy to Intermediate 2b, Example 30, by a process known from the literature (*J. Heterocyclic Chem.*, 18:603 (1981)).

d) 1-[4-(4-Bromobenzylamino)-2-ethyl-6-methylpyridin-5-yl]ethanone was prepared by the method described in Example 30 (Intermediate 2c) starting from 4-chloro-2-ethyl-6-methylpyridine and 4-bromobenzylamine. MS(ES+): 347/349.

2-Ethyl-6-methyl-5-acetyl-4-{4-[1-(3α,7α,12α-trihydroxy-10β,13β-dimethyl-17β-(3-carboxy-1-methylpropyl)hexadecahydrocyclopenta[a]phenanthren-3-yl)ethyn-2-yl]benzylamino}pyridine was prepared by the general process (see Example 1). MS(ES+): 700.

The present invention may be embodied in other specific forms without departing from its spirit or essential characteristics. The described embodiments are to be considered in all respects as illustrative only and not restrictive. The scope of the invention is, therefore, indicated by the appended claims rather than by the foregoing description. All changes which come within the meaning and range of equivalency of the claims are to be embraced within their scope.

We claim:

1. A compound of formula I

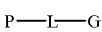

I wherein:

G is

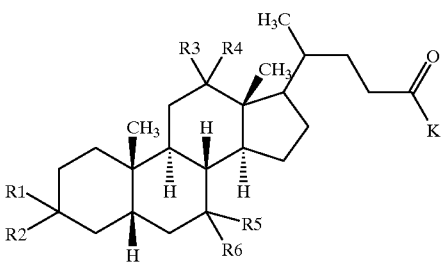

K is —OR(7), —NR(7)R(8), —HN—CH$_2$—CH$_2$—CO$_2$H, —HN—CH$_2$—CH$_2$—SO$_3$H, —NH—CH$_2$—CO$_2$H, —N(CH$_3$)CH$_2$CO$_2$H, —HN—CHR(9)CO$_2$H, or —Ocat, where cat is a cation;

R(7), R(8) are independently of one another selected from hydrogen, (C$_1$–C$_4$)-alkyl, phenyl, and benzyl, wherein an aromatic group is optionally substituted from 1 to 3 times by radicals independently of one another selected from F, Cl, CF$_3$, methyl, and methoxy;

R(9) is (C$_1$–C$_4$)-alkyl, benzyl, —CH$_2$—OH, H$_3$CSCH$_2$CH$_2$—, HO$_2$CCH$_2$—, or HO$_2$CCH$_2$CH$_2$—;

R(1) to R(6) are independently of one another selected from hydrogen, —OR(10), —SR(10), —NR(10)R(13), —OCOR(10), —SCOR(10), —NHCOR(10), —OPO(OR(10))$_2$, —OSO$_2$OR(10), —R(10), and one or more pairs of R(1) and R(2), R(3) and R(4), R(5) and R(6), wherein these pairs optionally form a carbonyl group, wherein only one of the radicals R(1) to R(6) is a bond to L;

R(10), R(13) are independently of one another selected from hydrogen, (C$_1$–C$_4$)-alkyl, phenyl, and benzyl, wherein an aromatic group is optionally substituted from 1 to 3 times by radicals independently of one another selected from F, Cl, CF$_3$, methyl, and methoxy;

L is (C$_1$–C$_{15}$)-alkyl, wherein one or more CH$_2$ units is optionally replaced by —CH=CH—, —C≡C—, —NR(11)—, —CO—, —O—, —SO$_2$—, or —S—;

R(11) is hydrogen, (C$_1$–C$_8$)-alkyl, R(12)—CO—, phenyl, or benzyl;

R(12) is hydrogen, (C$_1$–C$_8$)-alkyl, phenyl, or benzyl, wherein an aromatic group is optionally substituted from 1 to 3 times by radicals independently of one another selected from F, Cl, CF$_3$, methyl, and methoxy;

P is

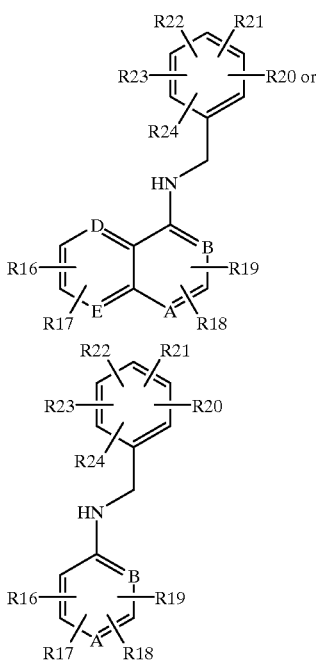

wherein:

A is N or CH;
B is N or CH;
D is N or CH;
E is N or CH;

R(16) to R(24) are independently of one another selected from hydrogen, F, Cl, Br, I, (C$_1$–C$_4$)-alkyl, CN, NO$_2$, NR(25)R(26), OR(25), OCOR(25), COR(25), COOR(25), CONR(25)R(26), SO$_2$R(25), SO$_2$OR(25), and SO$_2$NR(25)R(26), wherein an alkyl radical is optionally substituted one or more times by fluorine, and wherein only one of the radicals R(16) to R(24) is a bond to L; and R(25), R(26) are independently of one another selected from hydrogen, (C$_1$–C$_4$)-alkyl, phenyl, and benzyl, wherein an alkyl radical is optionally substituted one or more times by fluorine;

or a pharmaceutically acceptable salt thereof.

2. A compound of formula I as claimed in claim 1, wherein:

G is

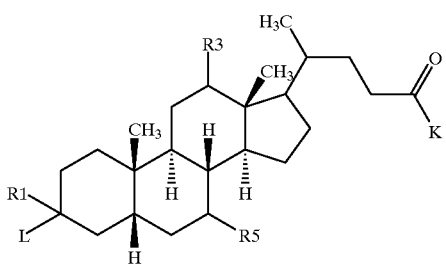

K is —OR(7), —NR(7)R(8), —HN—CH$_2$—CH$_2$—CO$_2$H, —HN—CH$_2$—CH$_2$—SO$_3$H, —NH—CH$_2$—CO$_2$H, —N(CH$_3$)CH$_2$CO$_2$H, —HN—CHR(9)CO$_2$H, or —Ocat, where cat is a cation;

R(7), R(8) are independently of one another selected from hydrogen, (C$_1$–C$_4$)-alkyl, phenyl, and benzyl, wherein an aromatic group is optionally substituted from 1 to 3 times by radicals independently of one another selected from F, Cl, CF$_3$, methyl, and methoxy;

R(9) is (C$_1$–C$_4$)-alkyl, benzyl, —CH$_2$—OH, H$_3$CSCH$_2$CH$_2$—, HO$_2$CCH$_2$—, or HO$_2$CCH$_2$CH$_2$—;

R(1), R(3), R(5) are independently of one another selected from hydrogen, —OR(10), NR(10)R(13), —OCOR(10), and —NHCOR(10);

R(10), R(13) are independently of one another selected from hydrogen, (C$_1$–C$_4$)-alkyl, phenyl and benzyl, wherein an aromatic group is optionally substituted from 1 to 3 times by radicals independently of one another selected from F, Cl, CF$_3$, methyl, and methoxy;

L is (C$_1$–C$_8$)-alkyl, wherein one or more CH$_2$ units is optionally replaced by —CH=CH—, —C≡C—, —NR(11)—, —CO—, —O—, or —SO$_2$—;

R(11) is hydrogen, (C$_1$–C$_4$)-alkyl, R(12)—CO—, phenyl, or benzyl;

R(12) is hydrogen, (C$_1$–C$_4$)-alkyl, phenyl, or benzyl, wherein an aromatic group is optionally substituted from 1 to 3 times by radicals independently of one another selected from F, Cl, CF$_3$, methyl, and methoxy;

P is

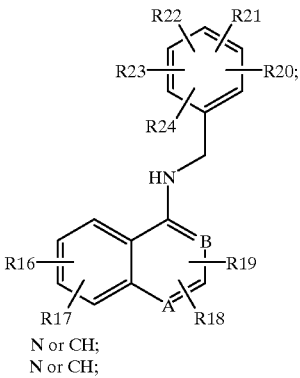

A  N or CH;
B  N or CH;

R(16) to R(24) are independently of one another selected from hydrogen, F, Cl, Br, (C$_1$–C$_4$)-alkyl, NR(25)R(26), OR(25), OCOR(25), COR(25), COOR(25), and CONR(25)R(26), wherein an alkyl radical is optionally substituted one or more times by fluorine, and wherein only one of the radicals R(16) to R(24) is a bond to L; and R(25), R(26) are independently of one another selected from hydrogen, (C$_1$–C$_4$)-alkyl, phenyl, and benzyl, wherein an alkyl radical is optionally substituted one or more times by fluorine;

or a pharmaceutically acceptable salt thereof.

3. A compound of formula I as claimed in claim 1, wherein:

G is

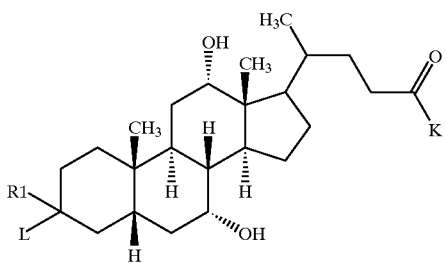

K is —OR(7), —NR(7)R(8), —HN—CH$_2$—CH$_2$—CO$_2$H, —HN—CH$_2$—CH$_2$—SO$_3$H, —NH—CH$_2$—CO$_2$H, —N(CH$_3$)CH$_2$CO$_2$H, or —Ocat, where cat is a cation;

R(7), R(8) are independently of one another selected from hydrogen, (C$_1$–C$_4$)-alkyl, phenyl, and benzyl, wherein an aromatic group is optionally substituted from 1 to 3 times by radicals independently of one another selected from F, Cl, CF$_3$, methyl, and methoxy;

R(1) is hydrogen, or —OH;

L is (C$_1$–C$_5$)-alkyl, wherein one or more CH$_2$ units is optionally replaced by —CH═CH—, —C≡C—, —NR(11)—, —CO—, —O—, or —SO$_2$—;

R(11) is hydrogen, (C$_1$–C$_4$)-alkyl, R(12)—CO—, phenyl, or benzyl;

R(12) is hydrogen, (C$_1$–C$_4$)-alkyl, phenyl, or benzyl, wherein an aromatic group is optionally substituted from 1 to 3 times by radicals independently of one another selected from F, Cl, CF$_3$, methyl, and methoxy;

P is

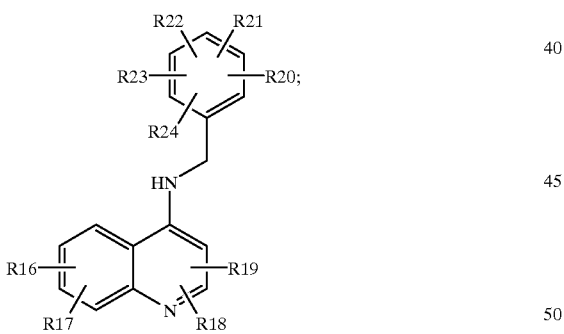

R(16) to R(24) are independently of one another selected from hydrogen, F, Cl, (C$_1$–C$_4$)-alkyl, NR(25)R(26), OR(25), OCOR(25), COR(25), COOR(25), and CONR(25)R(26), wherein an alkyl radical is optionally substituted one or more times by fluorine, and wherein only one of the radicals R(16) to R(24) is a bond to L; and R(25), R(26) are independently of one another selected from hydrogen, (C$_1$–C$_4$)-alkyl, phenyl, and benzyl, wherein an alkyl radical is optionally substituted one or more times by fluorine;

or a pharmaceutically acceptable salt thereof.

4. A compound of formula I as claimed in claim 1, wherein:

G is

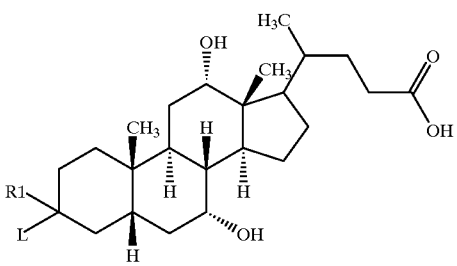

R(1) is hydrogen, or —OH;

L is (C$_1$–C$_5$)-alkyl, wherein one or more CH$_2$ units is optionally replaced by —CH═CH—, —C≡C—, —NR(11)—, —CO—, —O—, or —SO$_2$—;

P is

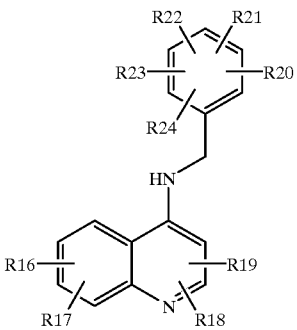

wherein:

R(16) to R(24) are independently of one another selected from hydrogen, F, Cl, (C$_1$–C$_4$)-alkyl, NR(25)R(26), OR(25), OCOR(25), COR(25), COOR(25), and CONR(25)R(26), wherein an alkyl radical is optionally substituted one or more times by fluorine, and wherein only one of the radicals R(16) to R(24) is a bond to L; and R(25), R(26) are independently of one another selected from hydrogen, (C$_1$–C$_4$)-alkyl, phenyl, and benzyl, wherein an alkyl radical is optionally substituted one or more times by fluorine, or a pharmaceutically acceptable salt thereof.

5. The compound of claim 1, wherein cat is at least one cation selected from an alkali metal ion, an alkaline earth metal ion, and a quaternary ammonium ion.

6. A pharmaceutical composition, comprising at least one compound as claimed in claim 1 together with a pharmacologically acceptable carrier.

7. The composition as claimed in claim 6, further comprising at least one lipid-lowering active ingredient.

8. A method of preparing a pharmaceutical composition in a form suitable for administration to a patient, comprising providing at least one compound as claimed in claim 1, mixing the at least one compound with a pharmaceutically suitable carrier to form a mixture, and converting said mixture into a form suitable for administration.

9. A method for the prophylaxis or treatment of gallstones, comprising administering to a patient in need thereof an effective amount of at least one compound as claimed in claim 1.

10. A process for preparing a compound as claimed in claim 1, comprising reacting a compound of formula IId:

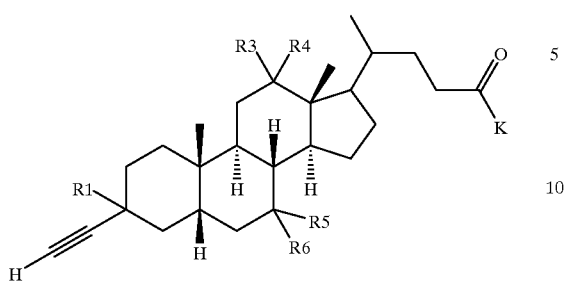
IId
wherein K, R(1), and R(3) to R(6) are defined as for formula I as claimed in claim 1, with a compound P—X of formula IIId:
P—X  IIId
wherein P is defined as indicated for formula I as claimed in claim 1, and X is halogen, in the presence of a Pd(0) catalyst and auxiliary base, forming a compound of formula IVd:
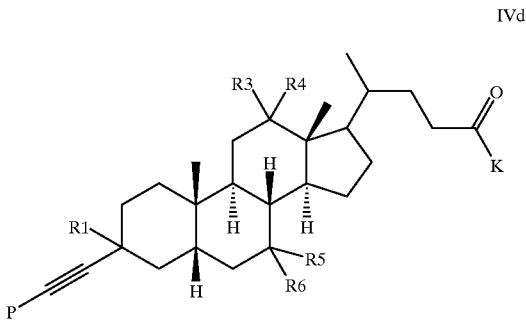
IVd
* * * * *

UNITED STATES PATENT AND TRADEMARK OFFICE
CERTIFICATE OF CORRECTION

PATENT NO. : 6,339,077 B1
DATED : January 15, 2002
INVENTOR(S) : Armin Hofmeister et al.

It is certified that error appears in the above-identified patent and that said Letters Patent is hereby corrected as shown below:

Column 59,
Line 15, insert "or" at right-hand margin for the column.

Signed and Sealed this

Twentieth Day of August, 2002

Attest:

JAMES E. ROGAN
Attesting Officer
Director of the United States Patent and Trademark Office